(12) United States Patent
Lund et al.

(10) Patent No.: US 11,911,139 B2
(45) Date of Patent: *Feb. 27, 2024

(54) SYSTEM AND METHOD FOR AUTOMATIC PERFUSION MEASUREMENT

(71) Applicant: Perfusion Tech APS, Roskilde (DK)

(72) Inventors: Morten Toft Lund, Copenhagen N (DK); Mads Holst Aagaard Madsen, Copenhagen Ø (DK)

(73) Assignee: Perfusion Tech APS, Roskilde (DK)

( * ) Notice: Subject to any disclaimer, the term of this patent is extended or adjusted under 35 U.S.C. 154(b) by 93 days.

This patent is subject to a terminal disclaimer.

(21) Appl. No.: 17/127,217

(22) Filed: Dec. 18, 2020

(65) Prior Publication Data

US 2021/0100461 A1 Apr. 8, 2021

Related U.S. Application Data

(63) Continuation-in-part of application No. 16/738,078, filed on Jan. 9, 2020, now Pat. No. 10,912,471, which (Continued)

(30) Foreign Application Priority Data

Jun. 14, 2018 (EP) .................................... 18177783

(51) Int. Cl.
*A61B 5/0275* (2006.01)
*A61B 5/1455* (2006.01)
(Continued)

(52) U.S. Cl.
CPC .......... *A61B 5/0275* (2013.01); *A61B 5/0059* (2013.01); *A61B 5/0261* (2013.01); *A61B 5/14551* (2013.01); *G01N 21/6486* (2013.01)

(58) Field of Classification Search
CPC ............ A61B 2505/01; A61B 2505/03; A61B 2505/05; A61B 2576/00; A61B 5/0059;
(Continued)

(56) References Cited

U.S. PATENT DOCUMENTS

| 8,976,481 B1 | 3/2015 | Zeng et al. |
| 9,610,021 B2 | 4/2017 | Dvorsky et al. |

(Continued)

FOREIGN PATENT DOCUMENTS

| JP | 2010-233939 A | 10/2010 |
| JP | 2016-521612 A | 7/2016 |

(Continued)

OTHER PUBLICATIONS

Mortensen et al ("Fluorescence guided intraluminal endoscopy in the gastrointestinal tract: A systematic review". World J Gastrointest Endosc. Oct. 16, 2020; 12(10): 388-400. (Year: 2020).*

(Continued)

*Primary Examiner* — Michael T Rozanski
(74) *Attorney, Agent, or Firm* — Julie K. Staple; Dinsmore & Shohl LLP

(57) ABSTRACT

The present disclosure relates to a system and a method for automatically measuring and assessing hemodynamics in tissue of an anatomical structure of a subject. In particular the present disclosure relates to continuously measuring and assessing hemodynamics in medical procedures using fluorescence imaging and wherein the administration of the fluorescent agent is controlled and automated. One aspect relates to a method of automatic perfusion assessment of an anatomical structure of a subject, the method comprising administration into a vein of a bolus corresponding to less than 0.005 mg ICG/kg body weight of a first fluorescence imaging agent.

21 Claims, 13 Drawing Sheets

Related U.S. Application Data is a continuation of application No. PCT/EP2019/065648, filed on Jun. 14, 2019.

(51) Int. Cl.
*A61B 5/00* (2006.01)
*A61B 5/026* (2006.01)
*G01N 21/64* (2006.01)

(58) Field of Classification Search
CPC ... A61B 5/0071; A61B 5/0261; A61B 5/0275; A61B 5/11; A61B 5/1128; A61B 5/14551; A61B 5/4216; A61B 5/4238; A61B 5/4255; A61B 5/6887; A61B 5/7207; G01N 21/6486; G16H 30/40; G16H 50/20; G16H 50/50
See application file for complete search history.

(56) References Cited

U.S. PATENT DOCUMENTS

| | | | |
|---|---|---|---|
| 10,912,471 B2* | 2/2021 | Lund | A61M 5/007 |
| 2010/0061604 A1 | 3/2010 | Nahm et al. | |
| 2010/0069759 A1 | 3/2010 | Schuhrke et al. | |
| 2012/0155735 A1 | 6/2012 | Friedman et al. | |
| 2014/0163403 A1 | 6/2014 | Lenox et al. | |
| 2016/0228579 A1 | 8/2016 | Ho et al. | |
| 2016/0262638 A1 | 9/2016 | Kamada et al. | |
| 2017/0128059 A1 | 5/2017 | Coe et al. | |
| 2017/0266398 A1 | 9/2017 | Murray et al. | |
| 2018/0028079 A1 | 2/2018 | Gurevich et al. | |
| 2018/0117183 A1 | 5/2018 | Reshetnyak et al. | |
| 2022/0192500 A1* | 6/2022 | Lund | A61M 5/007 |

FOREIGN PATENT DOCUMENTS

| | | |
|---|---|---|
| WO | WO-2009092162 A1 | 7/2009 |
| WO | WO-2018104552 A1 | 6/2018 |

OTHER PUBLICATIONS

Alander, J. T. et al. A review of indocyanine green fluorescent imaging in surgery, International Journal of Biomedical Imaging, Hindawi Publishing Corporation, vol. 2012, Article ID 940585, 26 pages.
Boni, L. et al. Indocyanine green-enhanced fluorescence to assess bowel perfusion during laparoscopic colorectal resection, Surg Endosc (2016) 30:2736-2742.
Degett, T. H. et al. Indocyanine green fluorescence angiography for intraoperative assessment of gastrointestinal anastomotic perfusion: a systematic review of clinical trials, Langenbecks Arch Surg (2016) 401:767-775.
James, D. R. C. et al. Fluorescence angiography in laparoscopic low rectal and anorectal anastomoses with pinpoint perfusion imaging—a critical appraisal with specific focus on leak risk reduction, Colorectal Disease, 2015 The Association of Coloproctology of Great Britain and Ireland. 17 (Suppl. 3), 16-21.
Kudszus, S. et al. Intraoperative laser fluorescence angiography in colorectal surgery: a noninvasive analysis to reduce the rate of anastomotic leakage, Langenbecks Arch Surg (2010) 395:1025-1030.
Liot, E. et al. Does near-infrared (NIR) fluorescence angiography modify operative strategy during emergency procedures? Surgical Endoscopy, 2018, Université de Genève. DOI: 10.1007/s00464-018-6226-9. PMID: 29770885.
Liu, J. et al. A Stable Optic-Flow Based Method for Tracking Colonoscopy Images, 2008 IEEE Computer Society Conference on Computer Vision and Pattern Recognition Workshops, Jun. 23-28, 2008, Anchorage, AK, USA, IEEE, 2008.
Nerup, N. et al: Quantification of fluorescence angiography in a porcine model. Langenbecks Arch Surg, published online Nov. 15, 2016.
Protyniak, B, et al. Intraoperative Indocyanine Green Fluorescence Angiography—An Objective Evaluation of Anastomotic Perfusion in Colorectal Surgery, Am. Surg. Jun. 2015; 81(6):580-4.
Rother, U.et al.: "Dosing of indocyanine green for intraoperative laser fluorescence angiography in kidney transplantation" Microcirculation, vol. 24, No. 8, Nov. 1, 2017, p. e12392.
Stein, D. E. "Colon Resection" Updated: Feb. 26, 2019; URL: http://emedicine.medscape.com/article/1891505-print.
Toens, C. et al: Validation of IC-VIEW fluorescence videography in a rabbit model of mesentereic ischaemia and reperfusion. Int J Colorectal Dis,;21:332-338, 2006.

\* cited by examiner

SYSTEM AND METHOD FOR AUTOMATIC PERFUSION MEASUREMENT

REFERENCE TO RELATED APPLICATIONS

This application is a continuation-in-part of U.S. patent application Ser. No. 16/738,078, filed Jan. 9, 2020, which is a continuation of PCT International Application No. PCT/EP2019/065648, filed Jun. 14, 2019, which claims priority to European Patent Application No. 18177783.0, filed Jun. 14, 2018. The entire content of each application is incorporated herein by reference.

FIELD OF THE INVENTION

The present disclosure relates to a system and a method for automatically measuring and assessing hemodynamics in tissue of an anatomical structure of a subject. In particular the present disclosure relates to continuously measuring and assessing hemodynamics in medical procedures using fluorescence imaging and wherein the administration of the fluorescent agent is controlled and automated.

BACKGROUND OF THE INVENTION

Injection of fluorescence imaging agents, aka fluorescent contrast agents, aka fluorescent agents, such as indocyanine green (ICG), to visualize blood flow and perfusion in anatomical structures was introduced many years ago, but the clinical use of this technology has been sparse. Today the dose of fluorescence agent has to be large enough to ensure a strong visual signal, which can easily be detected by the surgeon. Hence, assessment of for example perfusion in tissue based on fluorescence agents is based on the surgeons' visual inspection, i.e. it is largely subjective and can therefore vary between surgeons. An improved quantitative analytical approach to perfusion assessment in the gastrointestinal tract is disclosed in pending application PCT/EP2017/082204 entitled "System and method for assessing perfusion in an anatomical structure" and published as WO 2018/104552, from the same inventors. This application is hereby incorporated by reference in its entirety.

Existing methods for fluorescence imaging are typically based on only few perfusion measurements, maybe just one, conducted at critical points during the medical procedure, for example before a bowel resection and after creation of a bowel anastomosis. In order to create a visible fluorescence signal for the surgeon (or other medical professionals) a substantial dose of fluorescent agent is required. Such a substantial dose results in a visible burst in the fluorescence emission but also a period of wash-out of maybe 20-30 minutes where the fluorescence agent is still in the blood of the patient giving rise to a visible background fluorescent emission signal. This visible fluorescent emission signal in the wash-out period where the fluorescent agent is removed from the blood will often hinder that medical personnel initiate new fluorescence measurements in the wash-out period.

Today measurements employing fluorescence imaging involves many manual steps where the entire operation theatre is "paused" for several minutes. Typically it is the surgeon that decides to conduct a measurement involving fluorescent imaging, e.g. assessment of perfusion in the tissue of an anatomical structure. Initially the surgeon places the anatomical areas of interest correctly in the video picture received from a white light camera, e.g. an endoscopic camera. The surgeon then switches from normal white light to another camera which can capture the fluorescent light emitted from the areas of interest and the surgeon prompts an assistant to inject the fluorescent agent in a peripheral vein. After approx. 30 seconds of waiting the first fluorescent emission signal will appear and the surgeon waits for a number of minutes until it is decided that the visual fluorescent signal has been assessed sufficiently.

SUMMARY OF THE INVENTION

The manual administration and assessment of fluorescent imaging combined with only discrete measurements with long wash-out periods constitute significant practical limitations for the use of fluorescence image perfusion analysis in both elective and in emergency procedures. During emergency procedures it is crucial not to make a larger surgical intervention than necessary, as this increases surgery time and post-operative morbidity. At the same time, the surgeon cannot afford to leave an insufficiently perfused organ or part of the bowel, which can lead to tissue ischemia, necrosis, infections, anastomosis leakage and even death [Lioit et al. 2018]. One object of the present invention is therefore to make fluorescence imaging more susceptible for integration during emergency procedures.

In a first embodiment the present disclosure therefore relates to a system for automatic perfusion assessment of an anatomical structure of a subject, e.g. during medical procedures such as surgery. The system may be configured for controlling injection of a predefined amount of a fluorescence imaging agent into the blood of the subject. Injection can be provided by means of a controllable injection pump, which can be under control of the system. The injection pump may be part of the system, the system comprises at least one controllable injection pump for holding at least one fluorescence imaging agent. I.e. this injection pump may be configured for injecting a predefined amount of said fluorescence imaging agent into the blood of the subject. Preferably, the system is configured such that the predefined amount of said fluorescence imaging agent is repeatably injected at regular and/or predefined intervals. The system may further be configured for receiving and analysing a time series of fluorescence images, aka, video images, of the tissue of said anatomical structure following the injection of the fluorescence imaging agent. Based on this analysis at least one perfusion parameter of said anatomical structure can be determined.

By automating the fluorescence perfusion assessment we decrease the amount of time the surgeon and the rest of the operating theatre has to stand idle. Automation of the administration of fluorescence agent can further increase the use of fluorescence imaging making perfusion assessment much easier. This can lead to a modification of the operation strategy, for example creating a larger resection or making a resection where none was planned, or not making a resection altogether, even though one was planned to begin with.

In emergency situations surgery time is a limiting factor. And compared to elective surgery, the operation plan naturally will be more spontaneous. During such an emergency procedure, many perfusion assessments of the same or different tissues might be demanded within a short time. While one perfusion measurement can be performed within reasonable time, multiple measurements will quickly prolong the surgery time and become infeasible. This is an obstacle and a reason why these measurements are not used routinely today.

The presently disclosed system may therefore further be configured to control the injection pump to inject an initial small bolus of fluorescence imaging agent and subsequently analyse the fluorescence emission resulting from the initial bolus. This initial small bolus, preferably coupled with flushing with a physiological saline solution, should be selected according to the situation, i.e. what type of fluorescent agent is used and what is the configuration of the patient, e.g. age, weight, height, etc. However, an amount of less than 0.01 mg/kg body weight of the subject, i.e. less than 0.5 mg for a 50 kg patient and less than 1 mg for a 100 kg patient, is typically a good starting point, in particular if ICG is used.

The inventors have realized that the quantifiable fluorescence emission from the tissue of an anatomical structure is much less than the fluorescence emission that is visible to the human eye, for example by using computerized image analysis. I.e. much smaller doses, e.g. micro-doses, are possible because the fluorescence-signal intensity only has to be large enough to be measureable by computer vision and image analysis, and not by visual inspection by the surgeon. I.e. micro-doses of fluorescence agent can be administered to a subject and for example perfusion parameters can be determined therefrom.

The minimum bolus where a quantifiable fluorescence emission is provided can be estimated based on the situation. However, in order to find a more exact minimum effective bolus the presently disclosed system may further be configured to determine a subject specific minimum effective bolus of fluorescence imaging agent by controlling the injection pump to inject a series of boluses with varying amounts of fluorescence imaging agent according to a predefined criterion, such as incrementally increasing or incrementally decreasing, with a predefined time period between each bolus, analyse the fluorescence emission from the anatomical structure following the injection of each bolus, and determine the size of the minimum effective bolus that provides a quantifiable fluorescence emission from the anatomical structure.

By applying micro doses of fluorescent agents, the minimum time between consecutive measurements can be reduced significantly. And by determining the actual subject specific minimum bolus where a quantifiable fluorescence emission is provided, it is also ensured that the minimum wash-out period is provided which can minimize the duration between consecutive fluorescence measurements. This is because smaller doses are more rapidly removed from the blood.

Once the suitable bolus size that provides a quantifiable fluorescent signal and short wash-out periods that allow repeated injections of fluorescence imaging agent and fluorescent measurements have been found, the system can be configured to perform automatic measurements of perfusion parameters, e.g. with a predefined frequency determined by the wash-out period. The presently disclosed system may therefore further be configured to automatically 1) control the injection pump to inject a series of predefined boluses of fluorescence imaging agent, a predefined bolus such as the minimum effective bolus, with a predefined duration between each bolus, and 2) determine at least one perfusion parameter of said anatomical structure following the injection of each bolus.

The surgeon and other medical professionals in the operation theatre are now provided with continuous perfusion assessments of the relevant anatomical structure. The presently disclosed system and method thereby open for the possibility of providing continuous fluorescence imaging measurements, that can provide a range of perfusion parameters, as a sort of background information during the medical procedure. I.e. even though the surgeon has changed back to white light imaging during the actual surgical procedure, the fluorescence measurements can run automatically in the background without requiring manual intervention. Hence, valuable information about the perfusion can be provided to the medical personnel continuously and also with a time perspective, because the repeated perfusion measurements provides the possibility of following the development of the perfusion parameters over time. The use of automation and micro-doses in fluorescence perfusion measurements therefore opens for a whole new range of applications including regular use in both emergency and elective procedures to continuously assess viability of tissue and organs, such as the thyroid and parathyroid glands, the hepatic and bile ducts, the reproductive organs and urine bladder, tumours and their localization including lymph nodes and possible metastasis as well as assessment of skin/tissue/vessel perfusion in a variety of medical procedures, such as assessment of wounds and wound healing.

When measuring fluorescence perfusion in the traditional way, i.e. conducting a single measurement at one or more distinct points of the operation, this measurement will invariably be sensitive to measurement "noise". Both automation of fluorescence perfusion measurements and a decreased minimum interval between consecutive measurements make it more feasible to conduct multiple measurements of the same areas of interest during the medical procedure. The provision of multiple measurements is a great advantage because it reduces the effects of random noise that can arise from the stochastic diffusion of the fluorescent agents, the physiological variation of blood flow and distribution in the microcirculation of any anatomical region. Overall multiple measurements of the same areas of interest lead to better and physiologically correct perfusion assessments.

Should the surgeon wish to, the surgeon can still perform and save "normal"/full dose fluorescence perfusion measurements that provide a visual signal at critical points in the surgical procedure. These can e.g. be used as documentation of procedure quality in electronic patient records. After planning the first measurement, the surgeon can continue the medical procedure with only minimal breaks to either interpret the incoming perfusion values or change the areas under continuous assessment.

The inventors have further realized that the measurement and analysis of repeatable bolus injections can additionally be expanded from interpretation and quantification of a single inflow and/or a single outflow phase to analysis of oscillating fluorescence dynamics. These oscillating fluorescence dynamics may disclose physical perfusion characteristics hitherto unattainable without invasive measures.

The presently disclosed system and method may be configured for repeated injections of small boluses, such as the minimum bolus as disclosed herein, at regular intervals. These boluses may, depending on for example the injection time interval, lead to a cyclic variation that, when measured, takes the approximate form of an oscillating curve, e.g. a regularly oscillating curve such as a sinusoidal curve. In such a curve, the measured intensity signal is expected to increase with the inflow of the fluorescence imaging agent from a given bolus, and thereafter decrease during the wash-out phase of the bolus, until it once again increases at the subsequent bolus and so forth, resulting in a cyclic (sinusoidal) pattern.

Hence, the present disclosure further relates to a (computer implemented) method for detecting perfusion changes of an anatomical region of interest of a subject by image processing hemodynamics in at least a part of said anatomical region of interest in video images acquired from the subject. In one embodiment the method comprising the step of performing image analysis of at least one video sequence acquired during and/or after a plurality of boluses comprising fluorescence imaging agent are supplied to the subject. In that case it is an advantage if plurality of boluses are supplied according to a predefined pattern, such as in terms of frequency and/or dose, as also elaborated in further detail in the present disclosure. It is now possible to calculate subsequent perfusion parameters in one or more regions of interest based on the image analysis, i.e. as a plurality of doses are administered to the subject it is possible to continuously calculate perfusion parameters along with the provision of the boluses. With a plurality of perfusion parameters provided as a function of time (and bolus administration) it becomes possible to monitor the subsequent perfusion parameters to determine a change in perfusion in said region(s) of interest. This change in perfusion may be an indication that something is wrong.

Preferably the presently disclosed system is configured such that it can recognize parameters of the oscillating intensity curve, such as the frequency, the phase and/or the amplitude. The trained system can then in turn anticipate both the direction and regularity of the forthcoming signal dynamics. The system preferably uses measured values in order to recognize the oscillating pattern, such that the system thereafter is able to detect discrepancies between measured values and expected values. The system does not necessarily have to continuously measure the anatomical region of interest, instead it may only be able to measure at sporadic time intervals, such as in the case of the anatomic region of interest drifting in and out of focus of the recorded image. In these situations, the expected phase of the oscillating pattern at the measured time interval may be compared with the measured phase. The measured values may further be continuously used for updating the detected pattern, i.e. the expected values. Alternatively or additionally, injection parameters such as the bolus frequency, dose and flow rate may be used for determining the expected values, i.e. the oscillating pattern.

Discrepancies from the expected sinusoidal pattern may be caused by for example the onset of ischemic conditions in at least a part of an anatomical structure visible in the video image, or by a regional change in perfusion to a given area. An explanatory figure, demonstrating this change in dynamics due to the onset of ischemia in a human subject, is given in FIG. 12A and a more narrow zoom is given in FIG. 12B. As seen, it is possible to detect the transition from the regular oscillatory fluorescent signal to the ischemic flatline. It should however be noted that a change to the perfusion of the anatomical structure of interest may result in other measured patterns, additional to an ischemic flatline. An example is venous occlusion, wherein the outflow of blood from an anatomical area is blocked or reduced leading to a change in the oscillating dynamics due to congestion or pooling of fluorescent agents in the given area. As can be seen in FIG. 13C, while the cyclic oscillations cease the result is not a flatline.

Preferably, the presently disclosed system comprises tracking means and is able to run independently in the background, while a surgeon is only exposed to the visible white light signal, and thus only interrupted/notified by warning signals, during for example the detection of the onset of ischemia, which may be defined by an extended amount of time with ischemic conditions.

Following from what is disclosed above the present disclosure further relates to a method of automatic perfusion assessment of an anatomical structure of a subject, the method comprising administration into a vein of a bolus of about $\frac{1}{10}$ of the normal dose used for perfusion assessment. For Indocyanine green (ICG), the normal bolus is 0.1-0.3 mg/kg body weight. According to the present disclosure a bolus of less than 0.005 mg/kg body weight of a first fluorescence imaging agent can be used. For other fluorescence imaging agents described herein, the bolus is similarly reduced according to the present disclosure. In particular the present inventors have realized that even further reduced boluses of ICG are possible, in particular it has been shown that a bolus of less than 0.005 mg/kg body weight of a first fluorescence imaging agent like ICG can be used, more preferably less than 0.0049 mg/kg body weight, more preferably less than 0.0048 mg/kg body weight, more preferably less than 0.0047 mg/kg body weight, more preferably less than 0.004 mg/kg body weight, even more preferably less than 0.003 mg/kg body weight, yet more preferably less than 0.002 mg/kg body weight, and most preferably less than 0.001 mg/kg body weight of a first fluorescence imaging agent like ICG can be used. I.e. a bolus of less than 0.25 mg, or even less than 0.05 mg, for a 50 kg patient and less than 0.5 mg, or even less than 0.1 mg, for a 100 kg patient, is viable bolus that can be used for perfusion assessment, in particular if ICG is used. Usually the amount of the first fluorescence imaging agent is dissolved in a liquid.

The presently disclosed system and method can for example be used where the quantification of circulation through tissue can be decisive during surgery, i.e. in the field of visceral surgery in left-side colon and rectum resections, in stomach section transposition after oesophagus resection, in free small intestine transplants for interposition, anastomosis, etc. The presently disclosed approach can also be suitable for the detection of secondary perfusion disorders in the case of strangulated hernia or bridenileus. In heart surgery the presently disclosed system and method can be used to examine the efficiency of coronary bypasses and measure the perfusion during the procedure. In the field of plastic surgery it is possible to monitor the perfusion of transferred skin flaps, e.g. continuously, as well as to assess tissue damage in the case of traumas, and to assess wound healing such as in chronic wounds.

Another aspect of the present disclosure relates to continuous perfusion assessment in relation to repeated injections of a fluorescence active agent and monitoring the resulting oscillating curve. In addition to detect unforeseen changes to the perfusion, the system may be used for assessing the perfusion area of an artery. As an example a surgeon may consider to cut an artery as part of a surgical procedure. Before cutting the artery the surgeon may temporary restrict the perfusion through said artery and the presently disclosed approach can enable the visualization of the perfusion area of said artery within a short period of time, for example less than 1 minute. This may be valuable information for the surgeon during the continued surgical procedure. In a similar fashion, the system may be used for assessing the drainage area of a vein or a group of veins, lymph vessels, lymph nodes or other parts of the circulatory and/or lymphatic pathways. By temporarily restricting the blood flow through the vessel, the blood will pool up in the anatomical region which is normally drained by this vessel or group of vessels. This enables the visualization of the anatomical area which is drained by the vessel within a relatively short period of time, for example less than 2 minutes. This may provide important information to the surgeon, such as during the continued surgical procedure, in areas such as general surgery and plastic surgery, including wound and reconstructive surgery.

A further aspect of the present disclosure relates to a computer program, e.g. a computer program recorded on a storage medium, which is to be loaded into the memory of a computer, or the system as disclosed herein, which causes the computer/system to execute the steps of any of the methods disclosed herein.

A further aspect of the present disclosure relates to an imaging system, i.e. an endoscopic imaging system, comprising a processing unit configured to execute the steps of any of the methods disclosed herein.

BRIEF DESCRIPTION OF THE DRAWINGS

FIGS. 2B, 2D and 2F are close-ups of FIGS. 2A, 2C and 2E, respectively, where the slopes starts.

FIGS. 4B, 4D and 4F are close-ups of FIGS. 4A, 4C and 4E, respectively, where the curves have their maximum intensity.

FIGS. 5B, 5D and 5F are close-ups of FIGS. 5A, 5C and 5E, respectively, where the ICG is washed out.

DETAILED DESCRIPTION OF THE INVENTION

Figure 1A:
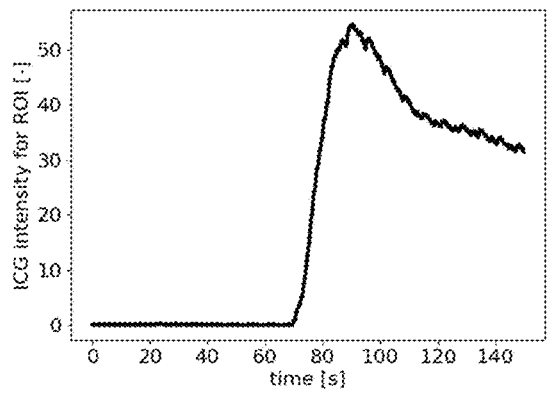
FIGS. 1A, 1C and 1E show examples of intensity curves after a bolus of ICG has been provided to a subject

In order to determine the subject specific minimum effective bolus, the background level of the setup can advantageously be determined, such that the minimum quantifiable fluorescent signal can be determined. Hence, the presently disclosed system is advantageously configured for 1) receiving a time series of images of the tissue of said anatomical structure prior to injection of the fluorescence agent, and 2) determining the background noise level therefrom. One or more regions of interest (ROI) can be selected, prior thereto of subsequent thereto. This selection of ROIs can be provided manually by the user, automatically by the system or semi-automatically, where the system suggests a number of ROIs whereupon the user can edit and/or move the suggested ROIs. A background noise level can be determined for each ROI.

As stated previously a minimum effective bolus can be determined, in particular a subject specific minimum effective bolus can be determined. The size of the minimum effective bolus can for example be determined based on the background noise level, in particular from the standard deviation of the background noise level. For example a minimum effective bolus can be determined as the bolus that provides a maximum intensity which is a predefined factor times the standard deviation of the background noise level. We note, said background noise level may or may not be close to zero in intensity. The background noise may also vary (e.g. as a result of a long sequence of micro boluses. However, the change in background noise is preferably on a much larger timescale, such as at least a factor 2, more preferably at least a factor 4, even more preferably at least a factor 6, most preferably at least a factor 10, times larger than the intensity change observed for a single injection.

Values from several ROIs can be provided and the intensity between different ROIs can vary significantly, in particular the maximum intensity. The minimum effective bolus can be determined as the bolus that provides a maximum intensity which is a predefined factor times the standard deviation of the background noise level. In one embodiment this must apply to all ROIs. However, there might be situations where an ROI selected does not provide a viable signal, e.g. if there is no perfusion in that part. In such a situation one or more of the ROIs can be left in the assessment of the minimum effective bolus.

The predefined factor mentioned above may be at least 5, more preferably at least 10, even more preferably at least 25, most preferably at least 50.

Once the minimum effective bolus, such as the subject specific minimum effective bolus, has been determined, that actual bolus that will be used in the continuous and repeated measurement procedure going forward may be this minimum effective bolus. However, in order to ensure that a usable signal is provided it may be decided that the actual bolus that will be used is a certain percentage of the minimum effective bolus. The actual bolus used may be less than the determined viable bolus, but in particular the actual bolus used may be larger than the minimum effective bolus, such as at least 125%, more preferably at least 150%, even more preferably at least 200% and most preferably at least 300% of the minimum effective bolus. It is however important to note that the actual bolus may vary over time, and does not have to be set at a constant percentage value of the minimum effective bolus. Instead, the actual bolus may change over time. This is for instance the case when an initial large actual bolus is injected followed by smaller actual boluses. In this way an initial large actual bolus, which may be between 125% and 375% of the minimum effective bolus, more preferably between 150% and 350% of the minimum effective bolus, even more preferably between 175% and 325% of the minimum effective bolus, most preferably between 200% and 300% of the minimum effective bolus, may be used to saturate the intensity signal. The initial large actual bolus may thereafter be followed by repeated injections of smaller actual boluses at a constant percentage value of the minimum effective bolus, such as around 100% of the minimum effective bolus.

When determining the subject specific minimum effective bolus, the boluses are injected with a time period between each bolus, preferably a predefined time period but possibly a time period which can be adjusted based on the measured fluorescence measurements. The time period can also be customized to the specific situation, e.g. the subject. At least initially the time period between injections will typically be in the order of 20-60 seconds, possibly even 20-40 seconds, or 20-30 seconds. In other instances the time period between injections will typically be in the order of 5-600 seconds, possibly even 30-300 seconds, or 90-120 seconds, at least when using ICG, because this is the normal duration from rise of the slope until the intensity has dropped sufficiently again.

The time period from injection of a fluorescence agent until a fluorescence emission can be detected varies between situations and may typically depend on for example tissue perfusion characteristics and blood flow characteristics but may further depend on other individual factors of the patient such as anatomical structures, tissue compositions and interaction dynamics, or possibly other factors such as the fluorescent agent, etc. This period can be estimated but it is advantageous if the specific time period is known. Hence, the presently disclosed system may further be configured to determine the subject specific conversion period defined as the time period from injection of a bolus of the fluorescence imaging agent to a rise of a fluorescence slope in the fluorescence emission from the anatomical structure.

The presently disclosed system may further be configured to determine a subject specific disruption interval defined as the time period from the rise of a fluorescence slope to the fluorescence emission equals the background noise, alternatively until the fluorescence emission falls below a number of standard deviations, such as 20, 10 or 5 times SD, from the background noise, i.e. the subject specific time period where there is a detectable fluorescence emission.

The presently disclosed system may further be configured to determine a subject specific rise+fall interval defined as the time period from the rise of a fluorescence slope, passing the maximum intensity and until the fluorescence emission falls below 50% of the maximum intensity or more preferably below 25%, even more preferably below 10%, yet more preferably below 5%, most preferably below 1% of the maximum intensity.

The presently disclosed system may further be configured to determine a subject specific injection interval defined as the time period from injection of the fluorescent agent, rise of a fluorescence slope, passing the maximum intensity and until the fluorescence emission falls below 50% of the maximum intensity or more preferably below 25%, even more preferably below 10%, yet more preferably below 5%, most preferably below 1% of the maximum intensity. Once the fluorescence emission has fallen below a certain intensity a new bolus can be detected for quantification of the fluorescence emission. I.e. the subject specific injection interval can be seen as the time that is necessary to wait between subsequent injections of micro-doses of fluorescent agent. However, as it takes some from time from injection of a subsequent bolus and until it reaches the anatomical structure, it can also be the subject specific rise+fall interval defined above that can be seen as the time that is necessary to wait between subsequent injections of micro-doses of fluorescent agent.

The properties of existing fluorescence agents such as ICG are rather well known and the waiting time between subsequent injections can also be predefined. The rise+fall interval defined above is typically in the order of 20-60 seconds, maybe even 20-40 seconds or 20-30 seconds. In another embodiment the rise+fall interval defined above is typically in the order of 5-600 seconds, maybe even 30-300 seconds or 90-120 seconds.

Instead of waiting for the fluorescence agent to wash-out from the blood, it may be possible to determine perfusion parameters following the injection of a new bolus of fluorescence agent before the prior bolus is removed/washed out. In particular this may be possible if a subsequent bolus is larger than a prior bolus such that it is also ensured that an increased amount of fluorescence agent is administered. Hence, the presently disclosed system may be configured to automatically 1) control the injection pump to inject a series of boluses with increasing or decreasing amounts, such as incrementally increasing or incrementally decreasing amounts, of fluorescence imaging agent with a predefined time period between each bolus, and 2) determine at least one perfusion parameter of said anatomical structure following the injection of each bolus. The incrementally increasing amounts can for example be starting from 100% and increasing linearly with 10% such as 110%, 120%, 130%, 140%, etc. Alternatively increasing with 25%, i.e. 100%, 125%, 150%, 175%, etc. Alternatively increasing with 50%, i.e. 100%, 150%, 200%, 250%, etc. Alternatively increasing with 100%, i.e. 100%, 200%, 300%, 400%, etc. Alternatively increasing exponentially, such as 100%, 200%, 400%, 800%, etc.

The incrementally decreasing amounts can for example be starting from 200% and decrease linearly with 10% such as 190%, 180%, 170%, 160%, etc. Alternatively decreasing with 25%, i.e. 200%, 175%, 150%, 125%, etc. Alternatively decreasing with 50%, i.e. 250%, 200%, 150%, 100%, etc. Alternatively decreasing with 100%, i.e. 400%, 300%, 200%, 100%, etc. Alternatively decreasing exponentially, such as 800%, 400%, 200%, 100%, etc.

Automatic System

The system presently disclosed may be configured for determining said at least one perfusion parameter in one or more regions of interest located in said anatomical structure and optionally in neighbouring anatomical structures. The system may be configured such that these regions of interest can be selected by a user of the system.

The presently disclosed system may further be configured for forwarding said at least one perfusion parameter for presentation on a display. I.e. such that the medical personnel can follow the development of the perfusion assessment during the medical procedure. This display can be white light picture, with said parameter(s) superimposed.

The presently disclosed system may further comprise at least one processor and memory having instructions stored thereon, instructions, when executed by the one or more processors, cause the system to carry out what is disclosed in here.

The injection pump, aka medication pump, may be part of the presently disclosed automatic perfusion assessment system. The injection pump may be configured for delivering a time-controlled periodic infusion of fluorescence agent to a target, such as the subject. The control of the injection pump may be provided by means of a programmable and/or controllable control unit. Hence, the control unit can be configured to automatically operate said injection pump to periodically infuse the fluorescent agent in boluses with a controllable and/or predefined amount fluorescent agent according to the bolus amounts disclosed herein and with of controllable and/or predefined duration between infusions. I.e. the system may mere be configured for controlling the injection pump, e.g. by means of the control unit configured for controlling the injection pump. Controllable injection pumps are commercially available, for example a KDS single-syringe pump (series 100) from Sigma-Aldrich, or a Legato 212 Two-Syringe Pump from World Precision Instruments, or the Fusion controllable syringe pumps from Chemyx.

The presently disclosed automatic system may be external to an existing fluorescent imaging system, i.e. merely configured to control the injection pump and receive time series of fluorescent images from the existing system for analysis, for example an external system such as an endoscopic and/or laparoscopic setup, such as the Novadaq Pinpoint endoscopic fluorescence imaging system, or the Novadaq Spy-Phi portable handheld imaging system, wherein the imaging unit and optionally the light source are incorporated in the system. Existing laparoscopic systems from for example Olympus, Stryker, Karl Storz or surgical robots from Intuitive are also options.

However, the presently disclosed system may also be a more complete fluorescent imaging system, e.g. an endoscopic and/or laparoscopic system, where one or more light sources for fluorescent excitation, and control thereof can be included. I.e. in the further embodiment the system further comprises at least one light source configured to provide excitation light to induce fluorescence emission from said first and/or second fluorescent agent in said anatomical structure. E.g. a near infrared light source e.g, for ICG) which can be attached directly to a camera. Likewise with the imaging unit, i.e. the system may comprise an imaging unit configured for recording at least one time series of the fluorescence emission from the anatomical structure. E.g. a digital video camera which allows the emission of the fluorescence agent to be recorded in real time, which means that perfusion can be assessed and documented in real-time. The imaging unit may further be configured for white light imaging such that normal images of the anatomical structure can be received and/or viewed, i.e. while recording the fluorescent signal with a separate camera simultaneously. This may be provided by an additional camera in the imaging unit.

One embodiment of the present disclosure therefore relates to a system for automatic perfusion assessment of an anatomical structure during a medical procedure of a subject comprising a controllable injection pump for holding at least one fluorescence imaging agent, at least one light source configured to provide excitation light to induce fluorescence emission from said fluorescent agent in said anatomical structure, an imaging unit configured for recording at least one video sequence of the fluorescence emission from the anatomical structure, wherein the system is configured to automatically control the injection pump, the light source and the imaging unit for injecting a predefined amount of said fluorescence imaging agent into the blood of the subject, inducing and analysing fluorescence emission from said anatomical structure following the injection of the fluorescence imaging agent, determining at least one perfusion parameter of said anatomical structure based on said analysis.

Intraoperative Fluorescence Imaging

Perfusion (e.g. blood flow) can be imaged intra-operative and assessed in real time using the near-infrared light from a surgical microscope and acquiring video of fluorescent light in the near-infrared region that is excited from a fluorescent vascular contrast agent that has been intravenously administered as a tracer. The state of perfusion during the operation can thereby be confirmed in real-time.

The presently disclosed system and method can provide enhanced information of tissue characteristics including location of superficial and deeper blood vessels, in particular if different fluorescent agents are used, because careful selection of different fluorescent agents provides the option of having perfusion information from different depths in the tissue.

During a medical procedure, e.g. diagnostic, screening, examining and/or surgical procedure involving fluorescence imaging a solvent comprising the fluorescent contrast agent, such as ICG, is injected intravenously and the molecules are excited by an infrared light source, e.g. a laser with a wavelength in the infrared wavelength range, e.g. around 780 nm. Fluorescent light with a wavelength of around 830 nm is then emitted from the excited contrast agent molecules and can be recorded with an imaging device, e.g. in the form of a camera. A filter can be provided to block the excitation light as the excitation intensity typically is much larger than the fluorescence intensity. The excitation intensity can be around 1 W per emission angle whereas the fluorescent power pr. pixel can be around 0.15 pW. In spite of the several orders of magnitude in difference, good Signal to Noise Ratio (SNR) can be achieved. The recorded fluorescent light provides an image of the perfusion in imaged tissue and makes it possible to see deeper lying blood vessels, due to a penetration depth of 5-10 mm for ICG. Since the ICG molecule is bound to proteins in the blood, the video images contain information about the level of perfusion—but that information can be difficult to quantify for the surgeon during the operation if only the acquired video images are seen.

In the system and method of the present disclosure the fluorescent contrast agent is selected from the group of: indocyanine green (ICG) and fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof.

Indocyanine green (ICG) is a cyanine dye used in medical diagnostics, it is far the most common dye used for perfusion assessment. It has a peak spectral absorption at about 800 nm. These infrared frequencies penetrate retinal layers, allowing ICG angiography to image deeper patterns of circulation than fluorescein angiography. ICG binds tightly to plasma proteins and becomes confined to the vascular system. It is administered intravenously and, depending on liver performance, is eliminated from the body with a half life of about 3-4 minutes by the liver to bile juice. ICG sodium salt is normally available in powder form and can be dissolved in various solvents; 5% (<5% depending on batch) sodium iodide is usually added to ensure better solubility. The sterile lyophilisate of a water-ICG solution is approved in many European countries and the United States under the names ICG-Pulsion, IC-Green and VERDYE as a diagnostic for intravenous use.

The absorption and fluorescence spectrum of ICG is in the near infrared region. Typically a laser with a wavelength of around 780 urn is used for excitation. At this wavelength, it is possible to detect the fluorescence of ICG by filtering out scattered light from the excitation beam.

The toxicity is ICG is classified as low but administration is not without risks, e.g. during pregnancy. It is known that ICG decomposes into toxic waste materials under the influence of UV light, creating a number of still unknown substances. I.e. it is within the interest of the patient that the dose of ICG used during fluorescence imaging is minimized, as demonstrated herein.

Fluorescein is another dye which is widely used as a fluorescent tracer for many applications. Fluorescein has an absorption maximum at 494 nm and emission maximum of 512 nm (in water). Hence, it would be suitable for use in combination with ICG because the absorption and emission wavelength of the two dyes are separated by several hundred nanometres.

Method of Automatic Perfusion Assessment

As stated previously the present disclosure further relates to a method for automatic perfusion assessment of an anatomical structure of a subject, the method comprising administration into a vein of a bolus of about 1/10 of the normal dose used for perfusion assessment. For Indocyanine green (ICG), the normal bolus is 0.1-03 mg/kg body weight. According to the present disclosure a bolus of less than 0.01 mg/kg body weight of a first fluorescence imaging agent can be used. For other fluorescent imaging agents described herein, the bolus is similarly reduced according to the present disclosure. As stated above the agent may be injected by a controllable injection pump, for example as a series of boluses with a predefined time between subsequent boluses. Following injection of each bolus the fluorescence emission from the anatomical structure can be measured.

The minimum bolus that provides a quantifiable fluorescence emission representative of the perfusion of the anatomical structure can be determined following administering a series of increasing boluses. The bolus may comprise incrementally increasing or incrementally decreasing amounts of the agent, for example the amount may increase or decrease in increments of 10% from one bolus to the subsequent bolus.

The interval between boluses can be between 5 and 600 seconds, such as between 5 and 300 seconds, such as between 10 and 180 seconds, such as between 10 and 140 seconds, such as between 10 and 90 seconds, such as between 15 and 80 seconds, for example between 20 and 70 seconds, such as between 30 and 60 seconds. In another embodiment the interval between boluses can be between 5 and 600 seconds, such as between 10 and 600 seconds, such as between 15 and 600 seconds, such as between 15 and 300 seconds, such as between 30 and 240 seconds, such as between 45 and 240 seconds, for example between 90 and 240 seconds, such as between 90 and 120 seconds. Preferably between 60 and 600 seconds, or between 120 and 600 seconds. The interval between boluses is preferably sufficiently long to allow measurement of a perfusion slope for each bolus in the anatomical structure, preferably wherein the perfusion slope includes a slope start and a washout slope.

For ICG the amount of fluorescence imaging agent is preferably between 0.0001 and 0.01 mg/kg body weight per bolus, such as between 0.001 and 0.01 mg/kg body weight per bolus. An initial amount of fluorescence imaging agent is advantageously at least 0.001 mg/kg body weight. Subsequent boluses may then increase by at least 0.001 mg/kg body weight from one bolus to the subsequent. For other types of fluorescence imaging agents the dose is preferably chosen based on its fluorescence relative to ICG. Therefore a fluorescence imaging agent having higher emission rates is preferably administered at a correspondingly lower dose. The dose may for example be substantially inverse linear to the quantum yield of the fluorescence imaging agent. The dose may further be based on the absorption and emission spectra relative to ICG.

The bolus is preferably a liquid volume of between 0.5 µL and 10 mL, such as from 0.5-5 mL.

In a preferred embodiment of the present disclosure a volume of isotonic solution (such as saline) is injected immediately following injection of a bolus of fluorescence imaging agent, for example wherein the volume of isotonic solution is 1-20 mL, such as 2.5-15 mL, for example 5-10 mL.

In a further embodiment of the present disclosure a second fluorescence imaging agent is administered, the second fluorescence imaging agent having an emission maximum differing from the emission maximum of the first fluorescence imaging agent by at least 50 nm, or by at least 100 nm. The first and second fluorescence imaging agents are preferably administered alternatingly. Advantageously the interval between administrations of different fluorescence imaging agents is half of the interval between subsequent administrations of the same fluorescence imaging agent.

In a further embodiment of the presently disclosed method a series of fluorescence images of the anatomical structure is formed for the assessment of perfusion. The fluorescence may be detected automatically by illuminating the anatomical structure with a light source capable of exciting the fluorescence imaging agent, and the emission is quantified through a series of fluorescence images of the anatomical structure.

The period between boluses is determined by a computer configured to detect the perfusion slope caused by each bolus. Further, the amount of fluorescence imaging agent in a bolus may be controlled by a computer configured to determine a minimum bolus corresponding to a minimum fluorescence emission representative of the perfusion of the anatomical structure. This computer may be part of the presently disclosed system.

In a further embodiment the perfusion assessment comprises localizing a perfusion complication in the anatomical structure. Hence, the perfusion assessment may be used in connection with a diagnostic or surgical procedure, for example the procedure comprises diagnostic laparoscopy, explorative laparoscopy, surgical laparoscopy with traditional laparoscopy, robotic surgery, and open surgery. The procedure may alternatively comprise anastomosis, such as intestinal anastomosis, wounds, plastic surgery, cardiac surgery or cancer.

A further embodiment of the present disclosure relates to a fluorescence imaging agent for use in the method disclosed herein. Yet a further embodiment relates to the use of a fluorescence imaging agent in the preparation of a medicament for use in a method of automatic perfusion assessment as disclosed herein.

In a further embodiment of the present disclosure the fluorescence imaging agent is repeatably injected. In certain cases, there may be a need for a longer phase, such as at least 2 minutes, preferably at least 3 minutes, even more preferred at least 4 minutes, yet even more preferred at least 5 minutes, almost most preferably at least 8 minutes, most preferably at least 10 minutes, wherein the fluorescence imaging agent is not injected, in order to allow for the fluorescence imaging agent to be washed out, such that the background level is reduced. Once the background level is reduced to an acceptable level, such as below a certain percentage of the maximum fluorescent intensity or until substantially no fluorescent can be measured, the injections of the fluorescence imaging agent may be continued.

The presently disclosed system may be configured to carry out the method of automatic perfusion assessment of an anatomical structure disclosed above. This may be provided by the system having at least one processor and memory having instructions stored thereon, instructions, when executed by the one or more processors, cause the system to carry out the presently disclosed method of automatic perfusion assessment of an anatomical structure.

Perfusion Parameters

Various parameters can be determined based on image analysis of fluorescence emission. It is typically intensity values vs. time that are extracted from the image analysis and these values can be used to generate a number of chronological change curves, and the shape of said chronological change curve(s) can be analysed. From this analysis relative and/or quantitative data for perfusion, blood volume and/or blood flow can be determined, i.e. based on results of the image analysis of the time series of fluorescence images, aka video sequences of fluorescence images. In particular the perfusion slope of the flow of the fluorescent contrast agent through at least one of the regions of interest can be determined. The perfusion slope is a key parameter because it is a direct indication of the perfusion in the imaged tissue.

The perfusion parameters can be determined from the fluorescent intensity values extracted one or more regions of interest, typically comprising tissue. The configuration of the regions of interest, e.g. size of the regions, number of regions, locations in the image, etc., can be provided automatically, semi-automatically or manually by the user, e.g. the doctor/surgeon. With at least some kind of manual intervention the user may be able to select additional regions of interest or remove existing regions of interest. Preferably also move one or more of the regions around in the image such the regions of interest are located in relevant areas of the image, preferably prior to shooting of a video sequence.

The perfusion slope can be determined from the fluorescent intensity values integrated over a region of interest comprising tissue. Initially before injection of a contrast agent, the curve will be a substantially flat line. After the contrast agent has been injected the region of interest will begin to fluoresce as soon as a bolus of the contrast agent molecules have been excited and reach the region of interest—the result is a substantially linearly increasing line. When the bolus of contrast agent molecules levels off, so will the fluorescent intensity in the region of interest and washout will begin where the amount of contrast agent molecules decrease (substantially linear) to zero.

But this is the idealized scenario and the curves can vary from time to time and from patient to patient and it is therefore important with robust definitions of the perfusion parameters such that they can be determined automatically on the fly to be repeatable and comparable.

The perfusion slope can be defined by the slope of the extracted intensity values from slope start to slope end. The perfusion slope can merely be determined as a linear fit to the curve. The challenge is to determine the start point (slope start) and the end point of the fit (slope end), in particularly in a real time situation. Slope start is the most important of the two and can be defined as the point in time where the slope exceeds a predefined first threshold. The first threshold can for example be determined by three parameters: a predefined factor k, and the mean and standard deviation (std) of intensity values prior to slope start or prior to supply of the fluorescent contrast agent. Slope start can then be defined as the time point where the slope exceeds the mean by k*std. Slope end can correspondingly be defined as the point in time, after slope start, where the slope is reduced by more than a predefined second threshold. The constant k can be determined based on the setup, but typically k will be in the range of 3-10.

However, advantageously the perfusion slope can be determined from a histogram in a parameter space binning all slopes after slope start and where the perfusion slope is determined as the most frequent value of the histogram. I.e. after slope start a slope value is calculated for all subsequent intensity points based on slope start. Slope end can then be deduced therefrom. The slope values calculated immediately after slope start can be assigned more weight in the histogram than later slope values because it is certain that the perfusion slope has initiated after slope start. E.g. the first 100 calculated slope values can be assigned weights of 100, 99, 98, . . . etc., respectively, in the histogram. If a higher constant k is selected, the initial values of the perfusion slope can be assigned even more weight. The histogram centred approach is very precise and can advantageously be used in a real-time or near-real-time situation.

Another parameter that can be determined is the washout slope which is an indication of the extinctive flow of the contrast agent, e.g. through at least one of said regions of interest. Whereas the perfusion slope typically is positive due to the increasing flow of the contrast agent, the washout slope is opposite (in sign) to the perfusion slope, i.e. typically negative. The washout slope can add information about the perfusion in the tissue. However, the washout slope may also be relevant as an indication of the function of organs such as the liver. Similar to the perfusion slope, the washout slope can be defined by the slope of said intensity values from washout start to washout end. Washout start occurs after slope end. The washout slope can be determined from a histogram in a parameter space binning all slopes after washout start and where the washout slope is determined as the most frequent value of the histogram. As described above for the perfusion slope, some of the calculated washout slope values may be assigned more weight in the histogram than others, in particular the initial values of the washout slope after washout slope start.

The max intensity reached can easily be determined, e.g. for each ROI. However, a more relevant parameter could be the max slope intensity which is the intensity where the intensity values begin to level off. The max slope intensity can be defined as the intensity value at slope end. A more precise definition could be the intensity value at the time point where the distance to the straight line, which has the perfusion slope as gradient and intersects the curve-point determined by slope start, exceeds a predefined limit, for example a limit based on e.g. the standard deviation of the perfusion slope. E.g. the max slope intensity can be where the intensity level differs from the perfusion slope by a predefined factor times the standard deviation of the perfusion slope.

The slope rise time might also be relevant and can be defined as the difference between the time point of the max slope intensity and slope start, i.e. how long does the contrast agent take to flow through, or accumulate in, the tissue, which can be an indication of the speed of the blood flow.

The relative perfusion slope can then be defined as the inverse of the slope rise time. A subject specific relative perfusion slope can then be defined as the relative perfusion slope times the maximum intensity of a region of interest where perfusion is at a local (or global) extrema. I.e. a perfusion parameter which is normalized to become a patient specific perfusion slope parameter.

Tracking

In a further embodiment tracking of movement of the anatomic structure, e.g. the gastrointestinal tract, in the time series of images, e.g. video images, is provided. Hence, the presently disclosed system and method can employ tracking, as exemplified below, in such that the perfusion parameters can be extracted from the same anatomical structure(s), and the same parts of the anatomical structure(s) in repeated/continuous measurements. This tracked movement of the anatomical structure, or at least a part thereof, can be used such that at least one of the regions of interest corresponds to the same part of the anatomical structure in the video images.

In particular with open surgery the camera can be moved around a lot during the procedure. Hence, ROIs that have been selected may completely disappear from the images during the procedure and during continuous perfusion measurements. Tracking as disclosed herein is also about recognizing when the relevant areas and/or anatomical structures are inside the images—and when they are not, such that perfusion parameters measured from totally different areas are not incorrectly compared.

The purpose of tracking is primarily to ensure that the data, e.g. pixel intensity values, is sampled from the same tissue area. Thus, if the anatomical structure moves in the image, tracking should ensure that any regions of interest as defined herein would correspondingly move to ensure that the sampled data for said regions of interest is intelligible. In that regard is does not matter whether it is the anatomical structure that physically moves, e.g. due to subject respiration and/or peristaltic movements, or it is the imaging device acquiring the images that moves relative to the anatomical structure. What matters is whether the imaged object moves inside the acquired images.

A further aspect of the present disclosure therefore relates more generally to a computer implemented method for image processing movements/dynamics of at least a part of the anatomical structure (e.g. during medical procedure) from video images representing at least an exterior portion of said anatomical structure, comprising the steps of:

selecting one or more regions of interest in at least one of said video images, at least a first of said regions of interest corresponding to part/subsection of the of the anatomical structure, tracking movement of the anatomical structure in said video images, and correlating said movement of the anatomical structure such that at least said first region of interest corresponds to the same part of the anatomical structure in said video images.

Tracking of objects in a sequence of images, such as a video sequence, can be provided in different ways. Roughly speaking there are at least two different approaches: Free Image Tracking (FIT), which is based on the input video feed only, and Object Based Tracking (OBT), wherein predefined and/or recognizable objects are attached to the object that is being tracked in the images.

Free image tracking can for example be provided by means of classifiers: based on the input image a classifier algorithm computes classifiers of the most recognizable features in the area surrounding a given ROI (for more ROIs each ROI will be assigned a sensitivity-region within which the tracking works for the given ROI). In one embodiment of the present disclosure movement tracking of the anatomical structure is provided by free image tracking, for example in the form of classifier based tracking comprising the step of determining classifiers of one more recognizable features in the video images, preferably in an area adjacent to or surrounding at least one of the regions of interest.

Free image tracking can also be based on colour based tracking: prior to the medical procedure, such as surgery, minimum one ROI of the object, such as an anatomical structure, such as the bowel, have been marked with a colour and/or tattoo, preferably a predefined colour or tattoo. The marking can be provided by for example the surgeon. If it is the actual ROIs that have been marked, a colour based algorithm can obtain the form of the marking and use this form as the specific region of interest. A colour based algorithm can be configured to initially perform a colour filtering and subsequently object identification. Based on the properties of the marker (primarily the colour) a target RGB- or HSV-index can be provided for the filtering. A filtering, for example in the form of a HSV-thresholding, can then be provided to obtain a Boolean map of the input image pixels and this Boolean map will only contain pixels covering the marker. The object identification can then be provided by for example a noise-filtering, such as by opening or closing based on Erosion/Dilation, in order to remove noise from the Boolean map. With these noise-filter(s) an improved Boolean map can be obtained with "filled" ROIs. I.e. the resulting Boolean map will be full of zeroes except for patches filled with ones (or vice versa) and each patch will correspond to a ROI.

Another example of free-image tracking is based on cross-correlation: After selection of the ROI images, typically "normal" white light images, of the area within each ROI is stored as initial reference for each ROI. These initial ROI references are then subsequently used as templates in a cross-correlation function applied, e.g. continuously and/or in real-time, as a tracking function for each ROI. The cross-correlation function can be a form of pattern recognition and can be seen as a measure of similarity as a function of the displacement of two images relative to one another, i.e. it can be quite suitable as tracking function. The actual tracking function can for example, at least initially, be limited to the areas adjacent to each ROI, because in most cases the actual movement will be periodical. During the medical procedure additional ROI images can be acquired and stored and the initial template can therefore be improved, maybe continuously improved, if these additional acquisitions of ROI images are used as a basis for a mean that becomes the new, and possibly final, ROI template used in the tracking. Such an improved template including information from several ROI images thereby comprises a time aspect. This can make tracking much better and/or more efficient. For example if bowel movement is tracked and the bowel during the procedure rolls back and forth. With only an initial template ROI used in the tracking, it can be more difficult to track this ROI in every position of the rolling movement, but if a mean template that is averaged over several templates from the rolling movement, it can be much easier to track the ROI in every position of the rolling movement.

In object based tracking one or more objects are physically attached to the target that must be tracked, e.g. the bowel. As the object(s) are typically predefined in terms of for example size, shape and colour, classifiers can be trained prior to the tracking, i.e. the tracking system used can be configured to automatically recognize (and thereby track) the predefined objects. In one embodiment of the present disclosure anatomical structure movement tracking is provided by object based tracking, such as by tracking the movement of one or more predefined objects attached to the anatomical structure.

As an example of object based tracking two (or more) spheres (or another geometrically well-defined object) can be attached to a 'top' part of the anatomical structure and one (or more) sphere on the lower/bottom part of the anatomical structure (seen from the imaging device). If the objects attached to the top part are different from the object(s) attached to the bottom part it will be easy to distinguish the top part from the bottom part. If the spheres emit a tracker they are furthermore easily recognizable and therefore easily trackable. They could for example contain a fluorescent agent such that the spheres are visible when excited. They can then be identified in the images by for example a Hough-circle-recognition (or another feature-extraction). They can also be coloured and identified by the colour recognition method described above. Since the 'top'/'bottom' object are predefined and therefore known beforehand it is easy to train classifiers for both types of objects. To train a classifier for an object a large database of pictures of said object can be used to train a classifier. The position of the 'top' and 'bottom' objects in the images can thereby be determined very precisely by using classifiers.

As the objects are fixed to the target, e.g. the tissue of the bowel, ROI's can be defined based on these objects (e.g. 'top' and 'bottom'). For example in the case when using four objects, the ROI corners could simply correspond to the four tracked object positions. In case of two objects a ROI could be defined between the two object-positions: e.g. a parallelogram which expands in the middle to half height—this determines the angles.

It should additionally be noted that tracking is not limited to determining the two dimensional position/coordinates of the region of interest. Instead tracking may be implemented in such a way as to determine the position/coordinates of the region of interest with respect to all three dimensions of an Euclidean space. Multiple imaging methods are known for the three dimensional reconstruction of an object. These include for example methods based on oblique illumination, wherein the object is illuminated from the side, microscopy techniques such as confocal microscopy, light sheet fluorescence microscopy, 3D deconvolution microscopy and other methods wherein the properties of a known object is used in order to acquire depth information. Additional methods for acquiring depth information are known to a person skilled in the art and may be used in combination with the presently disclosed system in order to accurately track the region of interest in three dimensions. The obtained depth information is preferably used by the system in the assessment of the measured perfusion metrics, for example by normalizing the measured fluorescence intensity based on the distance to the region of interest Perfusion Assessment Much valuable information can be provided from the perfusion parameters mentioned above. However, in order to qualify the perfusion parameters some kind of reference might be necessary.

In one embodiment video sequences acquired from different parts of the anatomical structure can be used to calculate perfusion parameters relating to each part and these perfusion parameters can be compared such that the perfusion in the different parts of the anatomical structure can be compared, i.e. the perfusion parameters obtained from one of the video sequences can be used as reference such that a quantitative assessment of the perfusion can be provided between the video sequences relating to different parts of the anatomical structure.

In another embodiment different regions of interest from the same video sequence can be selected such that the perfusion parameters relating to one of the regions of interest is used as a reference for the other regions of interest such that a quantitative assessment of the perfusion can be provided between the different regions of interest in the same video sequence. These different regions of interest can be selected such that they represent different parts of the anatomical structure or different and nearby anatomical structures, e.g. if the anatomical structure is the gastrointestinal tract different parts of the gastrointestinal tract could be the colon and the small intestine. E.g. the surgery may be performed on the colon but by comparing to the small intestine, which very often will be physically nearby the colon and thereby can be imaged during the video acquisition, a reference can be provided which is unaffected by the surgery. Another example is a prospective skin flap compared to healthy well-perfused skin in plastic surgery.

I.e. determining at least a first perfusion parameter, e.g. of the flow of the fluorescent contrast agent through at least a first of said regions of interest, said first perfusion parameter selected from the group of: the perfusion slope, the washout slope, the max slope intensity, the relative perfusion slope and the subject specific relative perfusion slope, and determining at least a second perfusion parameter, e.g. of the flow of the fluorescent contrast agent through at least a second of region of interest, said second perfusion parameter selected from the group of: the perfusion slope, the washout slope, the max slope intensity, the relative perfusion slope and the subject specific relative perfusion, wherein the first and second regions of interest represent different parts of the anatomical structure or different anatomical structures. Then perfusion of one of said different parts of the anatomical structures can be evaluated by comparing with the perfusion of at least one other of said different parts.

A further embodiment therefore comprises the steps of:
performing image analysis of at least the following two video sequences, each video sequence acquired after a fluorescent contrast agent has been supplied to the subject:
first video images representing at least a first part of the anatomical structure or at least a first anatomical structure, and
second video images representing at least a second and different part of the anatomical structure or at least a second and different anatomical structure,
calculating intensity values in one or more regions of interest based on the image analysis of the first video images and the second video images, and
determining the perfusion slopes of the flow of the fluorescent contrast agent through at least a first region of interest selected in the first video sequence and at least a second region of interest selected in the second video sequence.

A further embodiment more specifically relates to the anastomosis process where perfusion assessment can be an important indication of where to provide the resection and whether the final anastomosis has sufficient perfusion. A further embodiment therefore further comprises the steps of:
performing image analysis of two or more of the following video sequences, each video sequence acquired after a fluorescent contrast agent has been supplied to the subject:
a) video images acquired before intestinal resection, such as bowel resection,
b) video images acquired after resection but before anastomosis, and
c) video images acquired after anastomosis.
calculating intensity values in one or more regions of interest based on the image analysis, wherein at least a first of said regions of interest is the same region in said two or more video sequences, and
determining the perfusion slopes of the flow of the fluorescent contrast agent through at least the first region of interest based on said two or more video sequences.

Based on these two or more video sequences one or more of the following parameters can be determined based on said two or more video sequences: the washout slopes, the max slope intensities, the relative perfusion slopes and the subject specific relative perfusion slopes.

Having parameters from two (or more) video sequences acquired at different times during the medical procedure makes it possible to use the parameter(s) extracted from one video sequence as reference parameter(s). Hence, quantitative data for the perfusion in at least one of said regions of interest based on slope parameters can be determined from said at least two video sequences. The result is that quantitative and qualitative evaluation parameters can be provided to the surgeon during and after a medical procedure, such as gastric surgery, for example assisting in evaluation of whether an intestinal, e.g. bowel, resection looks promising.

Both during and after surgery the result can be evaluated almost instantly, e.g. assessing whether an anastomosis has sufficient perfusion. This may for example be carried out by comparison of perfusion parameters which have been obtained before, during and/or after the surgery, or continuously during the medical procedure in order to quantify perfusion changes. Tracking of movements can be key to accurate quantification of the perfusion changes, as it is one way of ensuring that it is the same regions of interest that are assessed regarding perfusion before, during and/or after surgery, or continuously during the medical procedure.

Thresholds can be provided which are specific to the perfusion parameters. Also an uncertainty can be associated with a given threshold. A threshold comparison can for example indicate whether the operation went well or if the perfusion according to the parameter(s) in question has dropped below a critical level. And for several perfusion parameters a "weighted average answer" can also be provided.

In one embodiment of the present disclosure the perfusion slope (and/or other perfusion parameters as described) is calculated from video sequences acquired before resection and acquired after resection but before anastomosis. The relationship between the two perfusion slopes is a measure of the difference in perfusion before and after resection. If the perfusion drops below a predefined threshold after resection a warning can be given. More information can be extracted if perfusion slopes are calculated before and after resection for two, three or more regions of interest—and these regions of interest are the same tissue regions imaged before and after resection.

Oscillating Dynamics

The inventors have further realized that the measurement and analysis of repeatable bolus injections can additionally be expanded from interpretation and quantification of a single inflow and/or a single outflow phase to analysis of oscillating fluorescence dynamics. These oscillating fluorescence dynamics may disclose physical perfusion characteristics hitherto unattainable without invasive measures.

The presently disclosed system and method may be configured for repeated injections of small boluses, such as the minimum bolus, at regular intervals. These boluses may, depending on for example the injection time interval, lead to a cyclic variation that when measured takes the approximate form of a sinusoidal curve. In such a curve, the measured intensity signal is expected to increase with the inflow of the fluorescence imaging agent from a given bolus, and thereafter decrease during the wash-out phase of the bolus, until it once again increases at the subsequent bolus and so forth, resulting in a cyclic (sinusoidal) pattern.

Preferably the system is configured such that it can recognize parameters of the oscillating intensity curve, such as the frequency and/or amplitude. The trained system can then in turn anticipate both the direction and regularity of the forthcoming signal dynamics. The system preferably uses measured values in order to recognize the oscillating pattern, such that the system thereafter is able to detect discrepancies between measured values and expected values. The measured values may further be continuously used for improving the pattern recognition, i.e. the expected values. Alternatively or additionally, injection parameters such as the bolus frequency, dose and flow rate may be used for determining the expected values, i.e. the oscillating pattern.

With the system anticipating the expected value, it is able to, at an early time point—ideally instantaneously, detect and alert the onset of ischemic conditions. The detection of ischemic conditions may be a function of the expected value(s) and the detected value(s), such as for example a threshold value.

Discrepancies from the expected sinusoidal pattern may be caused by for example the onset of ischemic conditions in at least a part of an anatomical structure visible in the video image, or by a regional change in perfusion to a given area. An explanatory figure, demonstrating this change in dynamics due to the onset of ischemia in a human subject, is given in FIG. 12A and a more narrow zoom is given in FIG. 12B. As seen, it is possible to detect the transition from the regular oscillatory fluorescent signal to the ischemic flatline. It should however be noted that a change to the perfusion of the anatomical structure of interest may result in other measured patterns, additional to an ischemic flatline. An example is venous occlusion, wherein the outflow of blood from an anatomical area is blocked or reduced leading to a change in the oscillating dynamics due to congestion or pooling of fluorescent agents in the given area. As can be seen in FIG. 13C, while the cyclic oscillations cease the result is not a flatline.

Such a system, as described herein, can observe and detect changes in the perfusion level of a given area in the video image within seconds. This can be detected in an area which has been observed for a prolonged time, such as many minutes, where the dynamics have been visualized continuously and the phase thus is well known. An explanatory figure highlighting the difference between signals one can expect to observe for ischemic/healthy tissue areas is shown in FIG. 12C. However, it can equally be determined in an anatomical area which has only been visualized during a short time interval, e.g. 10-20 seconds, as the described system is trained to expect and detect a certain phase of the described oscillating dynamic signal at a given time in the tissue, consisting of regular rises and falls in the time-intensity signal. Cf. FIG. 12D illustrating how it may look if the anatomic region of interest drifted in and out focus of the recorded image.

Preferably, the system comprises tracking means and is able to run independently in the background, while a surgeon is only exposed to the visible white light signal, and thus only interrupted/notified by warning signals. During for example the detection of the onset of ischemic conditions.

Another aspect of the present disclosure relates to continuous perfusion assessment in relation to repeated injections of a fluorescence active agent and monitoring the resulting oscillating curve. In addition to detect unforeseen changes to the perfusion, the system may be used for assessing the perfusion area of an artery. As an example a surgeon may consider to cut an artery as part of a surgical procedure. Before cutting the artery the surgeon may temporary restrict the perfusion through said artery and the presently disclosed approach can enable the visualization of the perfusion area of said artery within a short period of time, for example less than 1 minute. This may be valuable information for the surgeon during the continued surgical procedure. In a similar fashion, the system may be used for assessing the drainage area of a vein or a group of veins, lymph vessels, lymph nodes or other parts of the circulatory and/or lymphatic pathways. By temporarily restricting the blood flow through the vessel, the blood will pool up in the anatomical region which is normally drained by this vessel or group of vessels. This enables the visualization of the anatomical area which is drained by the vessel within a relatively short period of time, for example less than 2 minutes. This may provide important information to the surgeon, such as during the continued surgical procedure, in areas such as general surgery and plastic surgery, including wound and reconstructive surgery.

Anatomical Structure

The anatomical structure of the presently disclosed system and method may be an internal organ of the subject. The perfusion will then typically be assessed in the tissue of the external part of the organ. The anatomical structure may alternatively be (part of) the skin of the subject. The perfusion will then typically be assessed in the skin tissue.

Perfusion assessment of wounds are also highly relevant. Hence, the anatomical structure may comprise at least one wound which will be the subject of the perfusion assessment.

The anatomical structure may be the gastrointestinal tract, preferably including buccal cavity; pharynx; the small intestine including duodenum, jejunum, and ileum; the stomach, including esophagus, cardia, and pylorus; the large intestine including cecum, colon, rectum and the anal canal.

Gastrointestinal Tract

Complications related to the gastrointestinal tract are often related to local hemodynamics. I.e. a change in the normal hemodynamic conditions may be an indicator of increased risk of a complication. Perfusion assessment of the gastrointestinal tract, in particular in and near the surface of the gastrointestinal tract, such as the tissue of the gastrointestinal wall, can therefore be an important diagnostic tool when examining the gastrointestinal tract, e.g. for diagnosis or for localization of a complication, for example during diagnostic laparoscopy, explorative laparoscopy or surgical laparoscopy with traditional laparoscopy or robotic surgery, as well as in open surgery. Perfusion assessment is also important during the surgical procedure of creating an anastomosis which can be provided to establish communication between two formerly distant portions of the gastrointestinal tract. As an example intestinal anastomosis establishes communication between two formerly distant portions of the intestine and typically restores intestinal continuity after removal of a pathologic condition affecting the bowel. Intestinal anastomosis may for example be provided for 1) restoration of intestinal, such as bowel, continuity following resection of diseased intestine, and 2) bypass of unresectable diseased intestine, e.g. bowel. Certain paediatric conditions may also require intestinal anastomosis [6].

Resection of diseased bowel can be performed in the following settings:
  Bowel gangrene due to vascular compromise caused by mesenteric vascular disease, prolonged intestinal obstruction, intussusceptions, or *volvulus*
  Malignancy
  Benign conditions (e.g. intestinal polyps, intussusception, roundworm infestation with intestinal obstruction)
  Infections (e.g. tuberculosis complicated with stricture or perforation)
  Traumatic perforations
  Large perforations (traumatic) not amenable to primary closure
  Radiation enteritis complicated with bleeding, stricture, or perforation
  Inflammatory bowel disease, ulcerative colitis, or Crohn's disease that is refractory to medical therapy or associated with complications (e.g. bleeding, perforation, toxic megacolon, dysplasia/carcinoma)
  Chronic constipation, idiopathic slow transit constipation, or Hirschsprung's disease: Subtotal colectomy may be performed when the disease is refractory to medical therapy.

Bypass of unresectable diseased bowel can be performed in the following settings:
  Locally advanced tumour causing luminal obstruction
  Metastatic disease causing intestinal obstruction
  Poor general condition or condition that prevents major resection Paediatric conditions for which intestinal anastomosis may be required include the following:
  Congenital anomalies (e.g. Meckel diverticulum, intestinal atresia, malrotation with volvulus leading to gangrene, meconium ileus, duplication cysts, Hirschsprung's disease)
  Inflammatory conditions (e.g. necrotizing enteritis, enterocolitis, tuberculosis, enteric perforation)
  Other conditions (e.g. intussusception, angiodysplasia, polypoid disease, ascariasis)
  As a part of other surgical procedures (e.g. Kasai portoenterostomy, choledochal cyst, urinary diversions, pancreatic neoplasms)

Postsurgical complications in connection with anastomosis in the gastrointestinal tract are unfortunately frequent, often due to insufficient perfusion (capillary blood supply) at the anastomosis, i.e. the joining of the two parts of the tract. Insufficient perfusion may cause anastomotic leakage, which is a serious and frequent complication, for example in connection with colorectal surgery where more than 10% of the procedures result in complications. Within colon cancer surgery more than 30% of patients with anastomotic leakage die due to postoperative complications and approx. 25% of the remaining patients suffer from stoma for the rest of their lives. Risk factors associated with leakage include tension of anastomosis, tissue damage and in particular reduced blood perfusion.

The present disclosure therefore in one embodiment relates to performing image analysis of one or more video sequences representing at least a part of the gastrointestinal tract, for example acquired before, during and/or after surgery, in particular surgery involving the gastrointestinal tract. This may in particular apply to gastrointestinal surgery—the video sequence may therefore comprise at an exterior portion of at least a part of the gastrointestinal tract, preferably such that perfusion in at least a part of the gastrointestinal wall can be measured and assessed.

The gastrointestinal tract is an organ system within humans and other animals which takes in food, digests it to extract and absorb energy and nutrients, and expels the remaining waste as faeces and urine. The gastrointestinal tract can be seen as a tube that transfers food to the organs of digestion. The term gastrointestinal tract as used herein therefore includes the buccal cavity; pharynx; the small intestine including duodenum, jejunum, and ileum; the stomach, including esophagus, cardia, and pylorus; the large intestine including cecum, colon, rectum and the anal canal.

EXAMPLES

The intensity curves shown in the examples are results of injections of boluses with normal amounts of fluorescent agent, in these cases ICG. In the amount of ICG in each bolus was chosen such that fluorescence emission was visible to the human eye. The examples are provided to illustrate the various perfusion parameters that can be calculated following fluorescent imaging. These same parameters can to a large extent also be determined following injection of the much smaller doses, i.e. the micro-dose approach with possibly repeated and continuous measurements and related assessment of perfusion, which is disclosed herein.

Figure 1B:
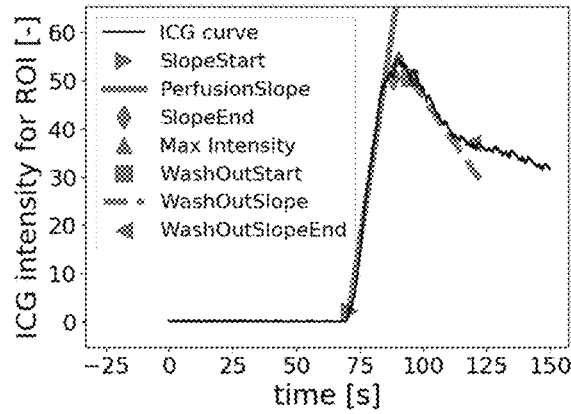
FIGS. 1B, 1D, and 1F show the corresponding intensity curves where the hemodynamic parameters perfusion slope, slope start, slope end max intensity, washout slope, washout start and washout slope end have been calculated and are indicated in the graphs.
Figure 1C:
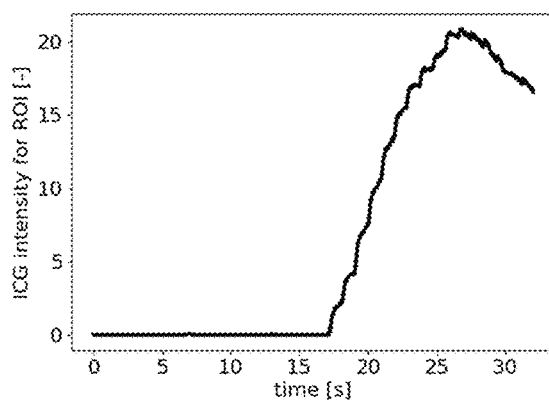
Figure 1D:
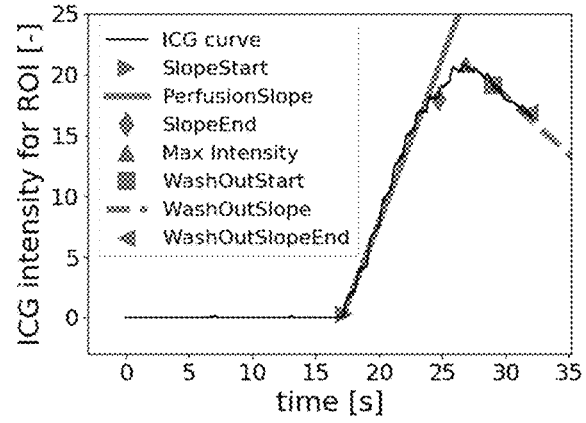
Figure 1E:
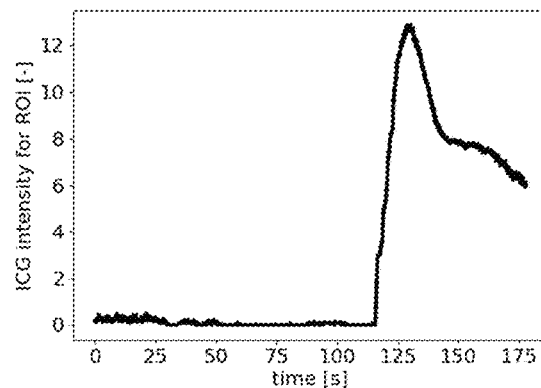
Figure 1F:
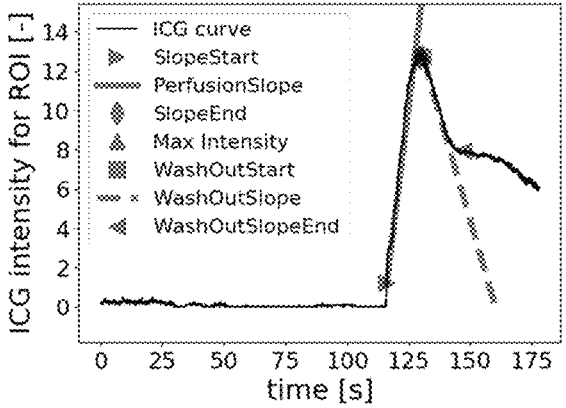

FIGS. 1A, 1C and 1E show examples of intensity curves acquired from tissue after a bolus of ICG has been provided to a subject, e.g. from a region of interest in a video sequence. The same kind of data could be obtained if another contrast agent was used. The intensity is substantially zero until a steep rise in intensity indicates the passage of ICG molecules in the imaged tissue, the ICG molecules being excited to fluoresce. The peak in intensity is followed by the gradual washout of the ICG molecules. The intensity is indicated with arbitrary units. FIGS. 1B, 1D, and 1F show the corresponding intensity curves where the hemodynamic parameters perfusion slope, slope start, slope end max intensity, washout slope, washout start and washout slope end have been calculated and are indicated in the graphs.

Figure 2A:
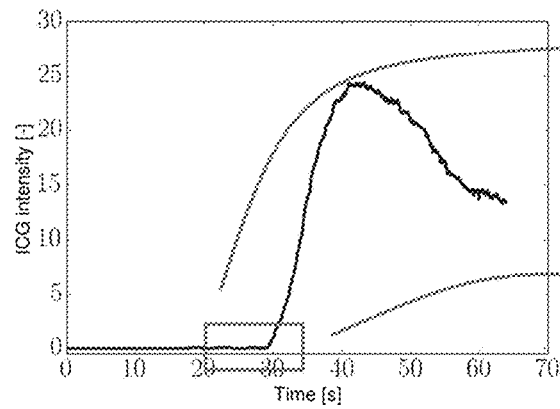
FIGS. 2A-2F show three examples illustrating the herein disclosed approach of determining the point in time where the perfusion slope starts, i.e. slope start.
Figure 2B:
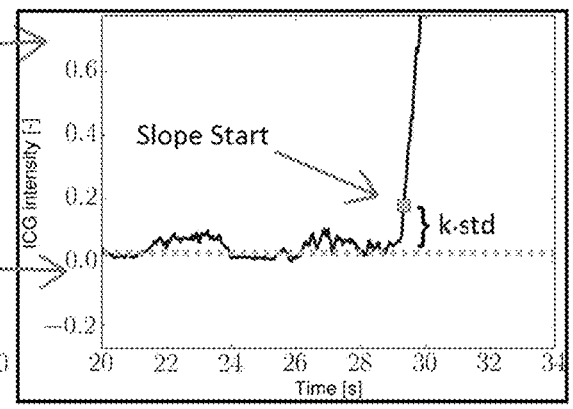
Figure 2C:
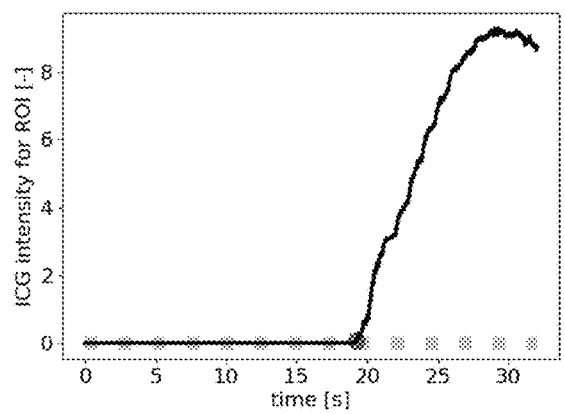
Figure 2D:
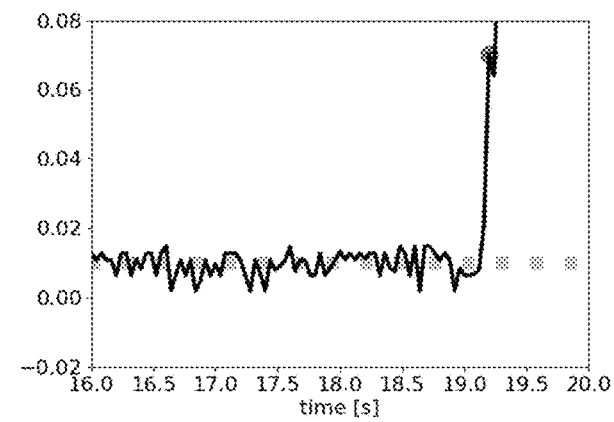
Figure 2E:
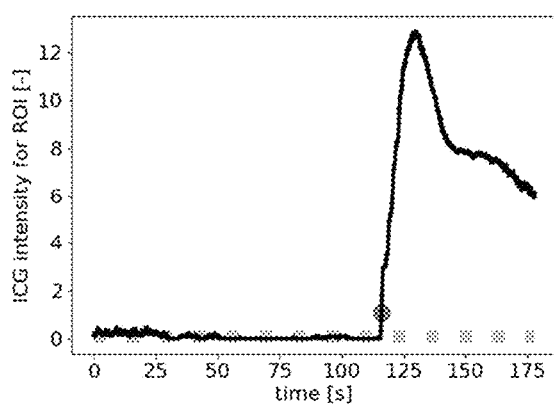
Figure 2F:
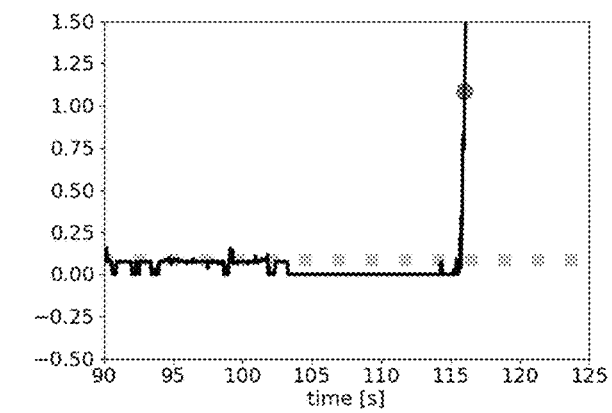
Figure 3A:
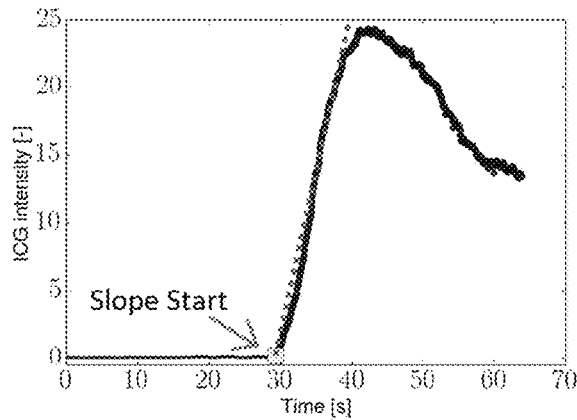
FIGS. 3A-3F show three examples illustrating the herein disclosed approach of determining the perfusion slope based on histogram data.
Figure 3B:
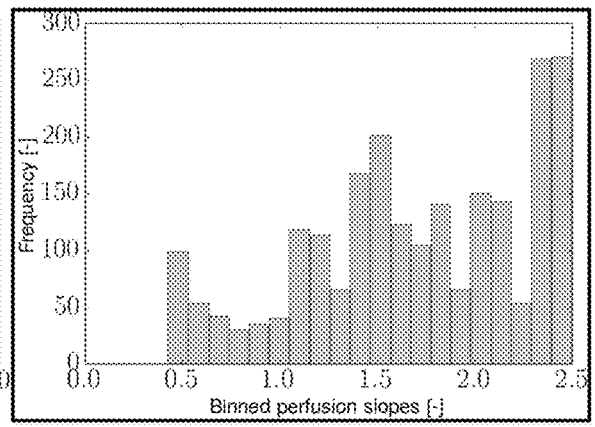
Figure 3C:
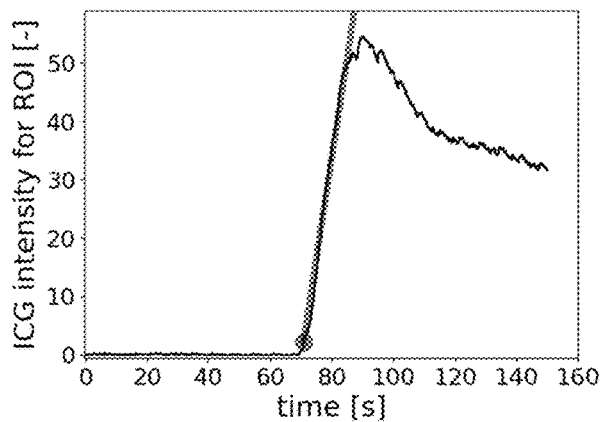
Figure 3D:
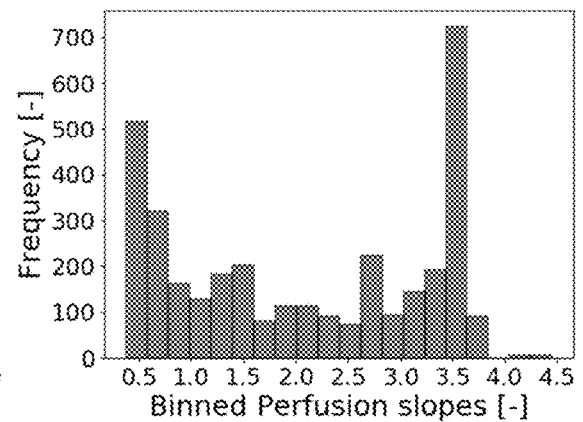
Figure 3E:
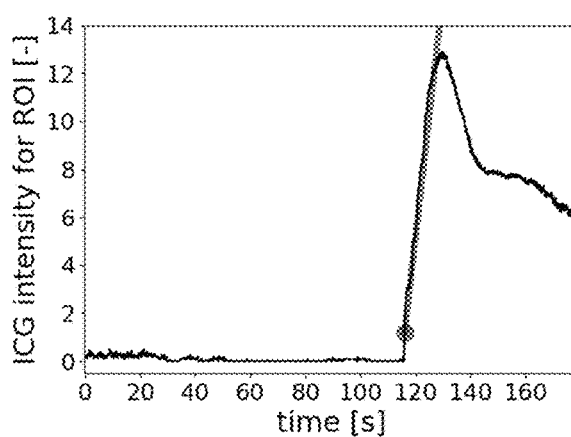
Figure 3F:
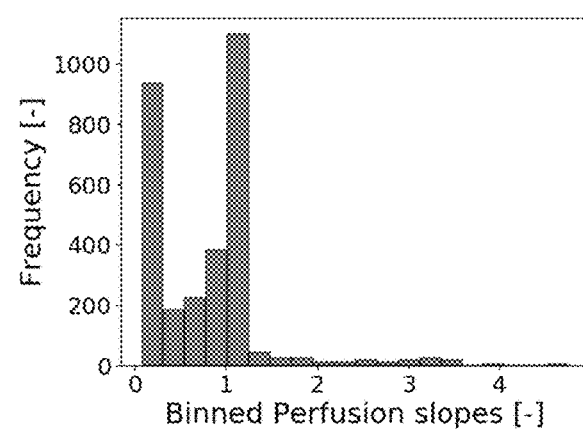

FIGS. 2A-2F show three examples illustrating the herein disclosed approach of determining the point in time where the perfusion slope starts, i.e. slope start. FIGS. 2B, 2D and 2F are close-ups of FIGS. 2A, 2C and 2E, respectively, where the slopes starts, i.e. the graphs to the right show a close-up of the curve to the left where the slope start is more detailed. Slope start is seen to be defined as the time point where the slope exceeds the mean by k*std, where k is a predefined constant and std is the standard deviation of intensity values prior to slope start. The slope start is indicated as a circle in FIG. 2B.

FIGS. 3A-3F show three examples illustrating the herein disclosed approach of determining the perfusion slope based on histogram data. The graphs to the left shows intensity curves, where FIG. 3A corresponds to FIG. 2A and FIG. 3E corresponds to FIG. 2E. The slope starts are indicated, by an arrow in FIG. 3A and by circles in FIGS. 3C and 3E. From slope start and to the end of the intensity curve all possible slopes of the intensity curve have been calculated. All the calculated slopes are collected and binned in the histograms shown to the right. The perfusion slopes are defined as the most frequent value of the histograms, i.e. the highest histogram bin. The calculated perfusion slopes of each of the intensity curves in FIGS. 3A, 3C and 3E, i.e. the highest histogram bin in FIGS. 3B, 3D, and 3F, respectively, are marked by straight lines in FIGS. 3A, 3C and 3E.

Figure 4A:
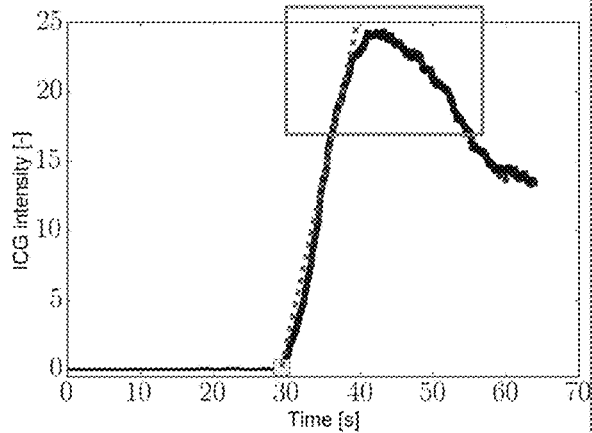
FIGS. 4A-4F show three examples illustrating the herein disclosed approach of defining and determining the max slope intensity.
Figure 4B:
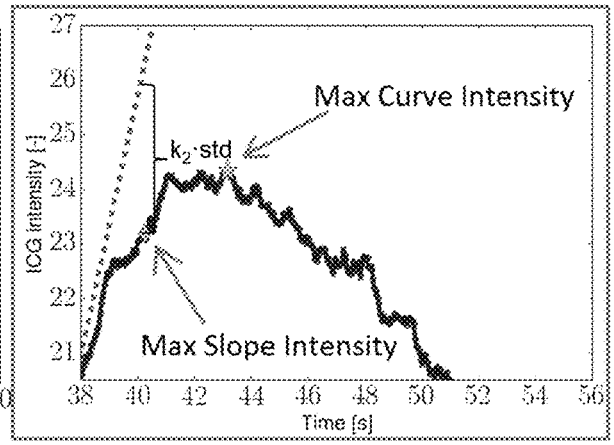
Figure 4C:
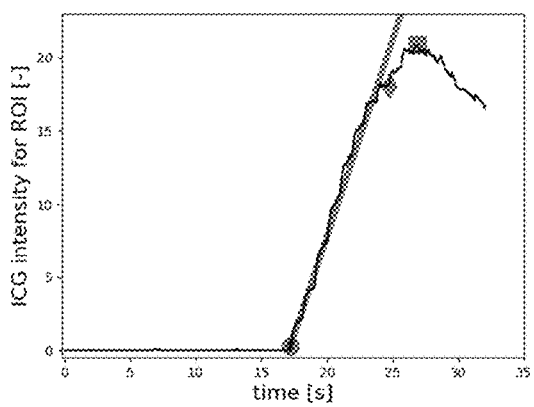
Figure 4D:
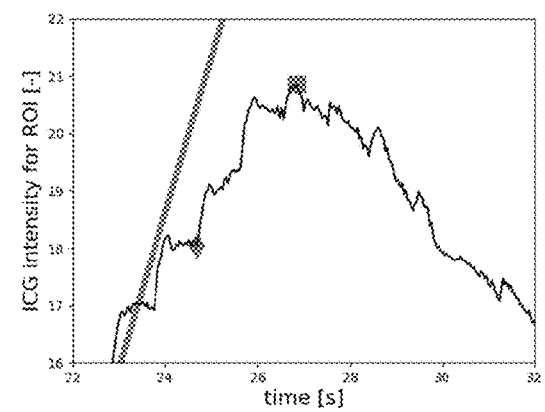
Figure 4E:
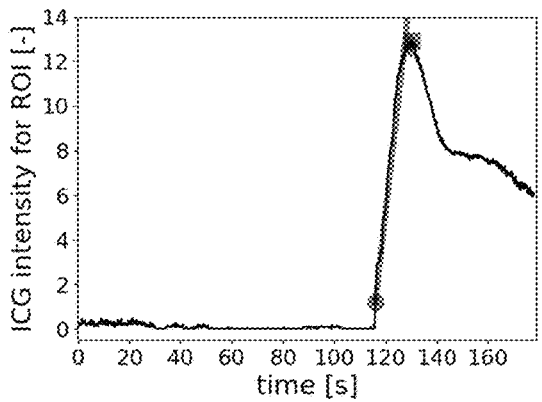
Figure 4F:
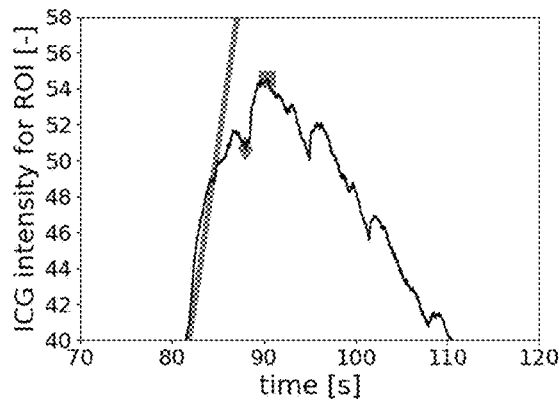

FIGS. 4A-4F show three examples illustrating the herein disclosed approach of defining and determining the max slope intensity. FIGS. 4B, 4D and 4F are close-ups of FIGS. 4A, 4C and 4E, respectively, where the curves have their maximum intensity. The maximum intensity of the curve is indicated by a star in FIG. 4B and by a square in FIGS. 4D and 4F along with the max slope intensity, which is indicated as a diamond in the figures. The max slope intensity is defined as the intensity value at the time point where the distance to the perfusion slope exceeds a predefined limit, for example a limit based on constant ($k_2$) times the standard deviation of the perfusion slope. As seen in FIG. 4 there can be significant differences in time and intensity between the maximum intensity of the curve and the max slope intensity. The slope rise time can be defined as the difference between peak (maximum) intensity of the curve and slope start. But as illustrated here the slope rise time defined as the difference between max slope intensity and slope start gives a more relevant definition of the slope rise time.

Figure 5A:
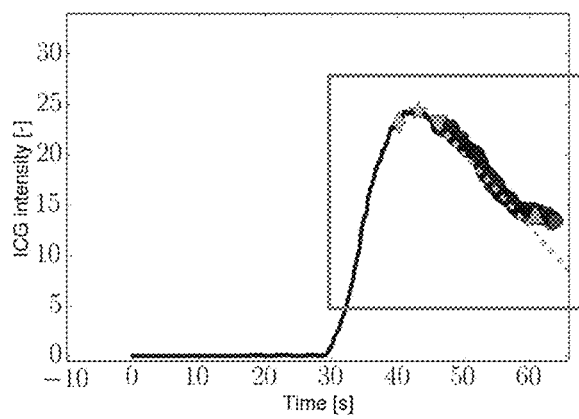
FIGS. 5A-5F show three examples illustrating the herein disclosed approach of analysing the washout of the fluorescence contrast agent.
Figure 5B:
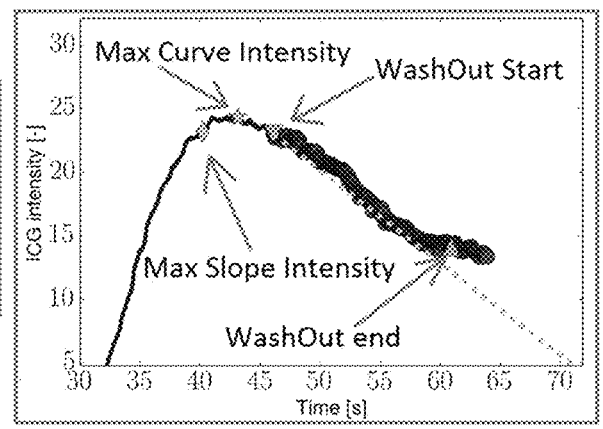
Figure 5C:
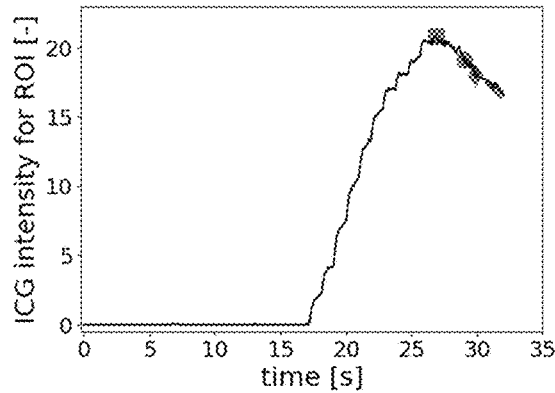
Figure 5D:
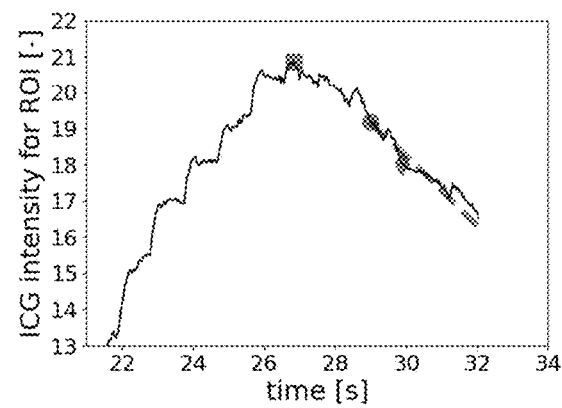
Figure 5E:
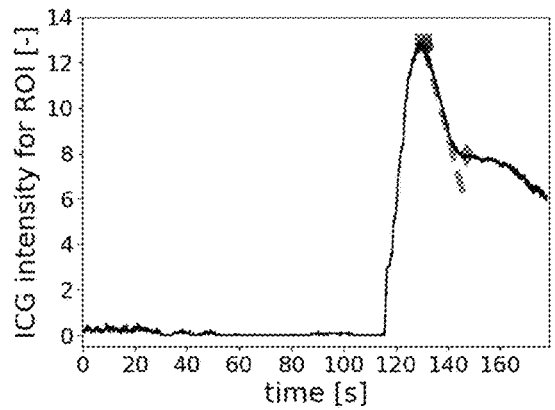
Figure 5F:
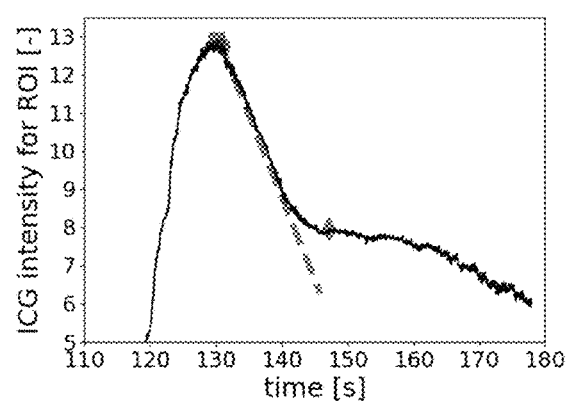

FIGS. 5A-5F show three examples illustrating the herein disclosed approach of analysing the washout of the fluorescence contrast agent. The intensity curves are the same as in FIG. 4. FIGS. 5B, 5D and 5F are close-ups of FIGS. 5A, 5C and 5E, respectively, where the ICG is washed out. In the graphs to the left the max intensities have been indicated by a star in FIG. 5A and by a square in FIGS. 5C and 5E. A close-up of the washout part is shown in the graphs to the right. The washout data has been analysed the same way as the perfusion slope and all possible washout slopes have been calculated. Similar to the above exemplified determination of the perfusion slope, the washout slopes can be binned and sorted in a histogram (not shown) in order to select the washout slope with the highest frequency. Washout start is typically after the max intensity of the curve. In this example washout starts are defined as being symmetric to the max slope intensity around the max curve intensity. Washout end is in this example determined the same way as the above exemplified determination of max slope intensity, i.e. when the intensity differs from the washout slope by a predefined constant times the standard deviation of the washout slope.

Figure 6A:
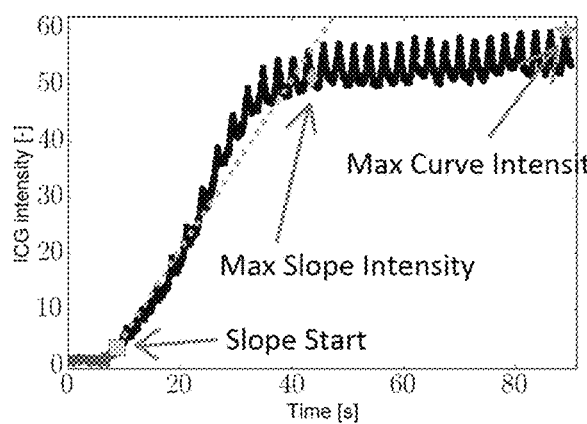
FIGS. 6A-6D show analysis of two additional fluorescence measurements using ICG illustrating the robustness of the presently disclosed analytical approach.
Figure 6B:
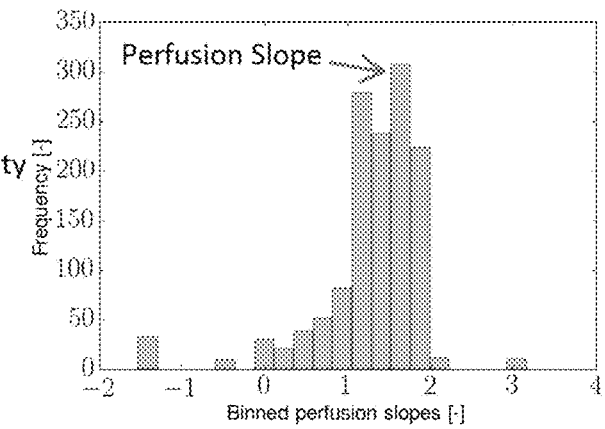

FIGS. 6A-6D show analysis of two additional fluorescence measurements using ICG illustrating the robustness of the presently disclosed analytical approach. The first in FIG. 6A shows the intensity data, slope start, the calculated perfusion slope (dotted line), max slope intensity and max curve intensity. The graph to the right shows the histogram with binned perfusion slope data. The intensity data is seen to be less stable than the other intensity curves disclosed herein with many local variations and no clear decrease in intensity after the perfusion slope. There will be a washout of the ICG molecules, but the data shown here do not include that part. FIGS. 6A and 6B illustrate that the exemplified approach disclosed herein is a very robust procedure that can be used for automatic and real-time determination of the perfusion slope and the other perfusion parameters derived therefrom. FIG. 6A also shows the large difference between the time points of the max slope intensity and the max curve intensity. The slope rise time derived from the max slope intensity is seen to be a much more relevant parameter to characterize the passage of the ICG bolus.

Figure 6C:
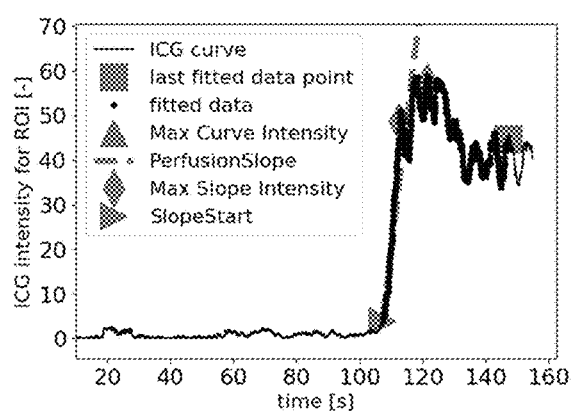
Figure 6D:
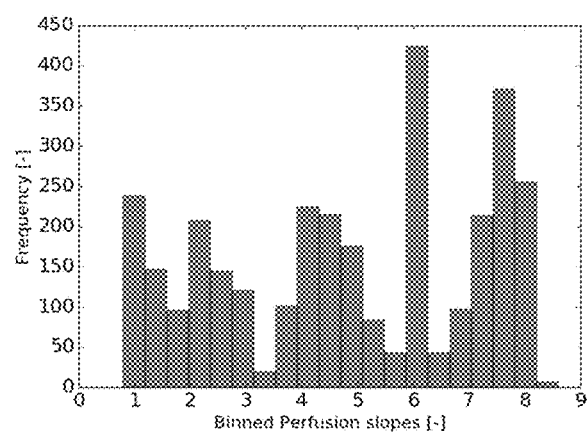

The second in FIG. 6C shows also unstable intensity data and all the calculated perfusion slopes are spread over a large interval as seen in the corresponding histogram in FIG. 6D. But by selecting the histogram bin with the highest frequency, relevant and precise perfusion slope parameters can nevertheless be extracted from the data, providing another example of the robustness of the presently disclosed approach.

Figure 7:
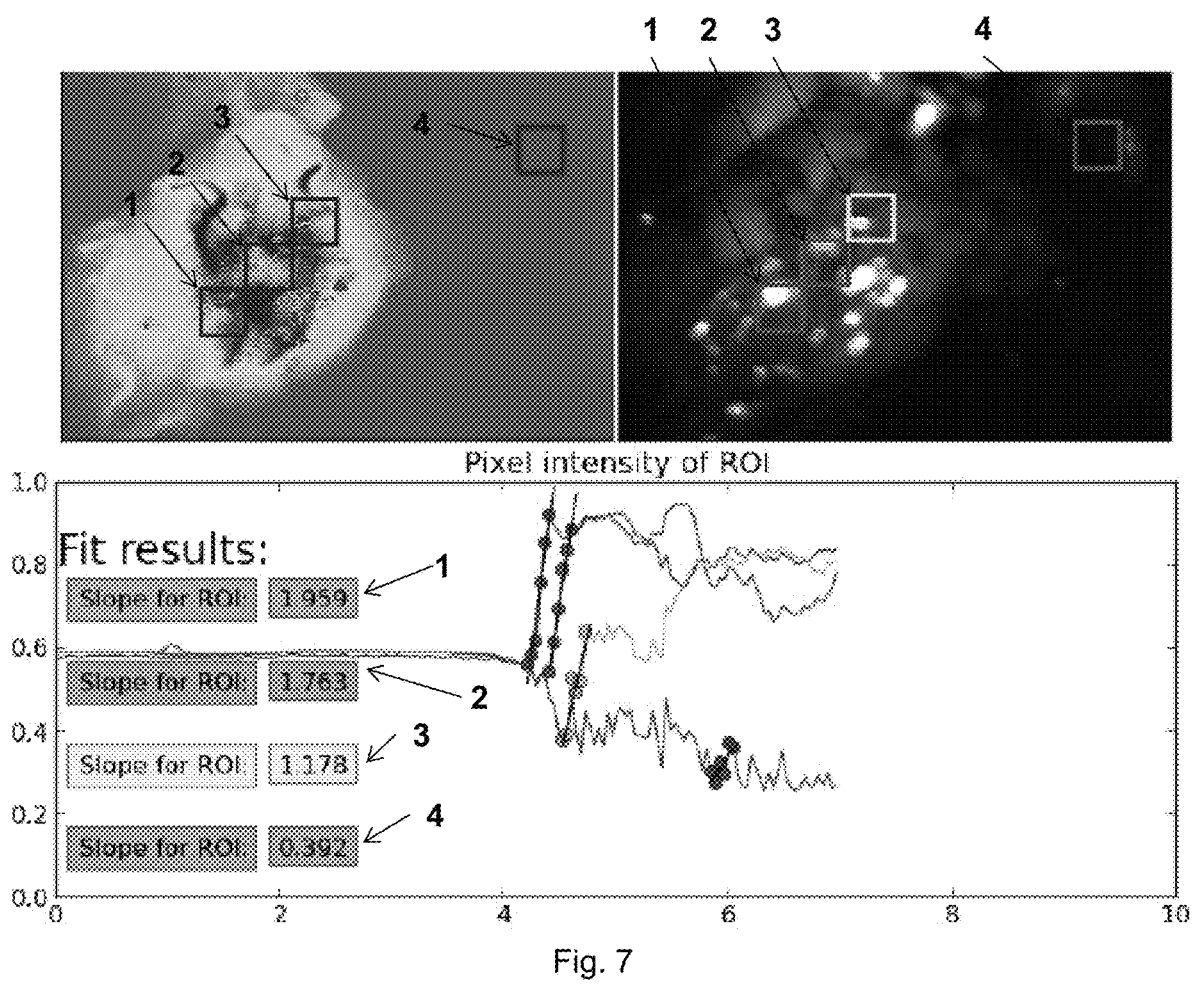
FIG. 7 shows an output video frame acquired during bowel surgery, four different regions of interest and analysis thereof.

FIG. 7 shows an output video frame from a video sequence acquired during bowel surgery. The upper right corner shows the raw footage (i.e. one frame) from the operation acquired during ICG bolus passage. The upper left corner shows the same video frame after image processing and the tissue perfusion is now much more clearly seen. As pointed out in the figures four regions of interest (1, 2, 3, 4) are indicated in the video frame. The graph below shows the mean pixel intensity of the four regions of interest plotted as a function of time (seconds) vs. normalized intensity. Perfusion slopes are calculated for the four ROIs (1, 2, 3, 4) and shown in the graph as straight lines.

When looking at only the two upper video frames, it is impossible for the surgeon to identify whether all of ROIs 1, 2 and 3, are equally and adequately perfused, e.g. whether the regions 1, 2 and 3 would be equally suited to place an anastomosis. This is also seen in the graph below after ~70 seconds, where the pixel intensities of ROI 1, 2 and 3 are similar. But by applying the herein disclosed approach of determining the perfusion slopes of the different ROIs, objective perfusion measures can be provided to the surgeon instantly. In the example in FIG. 7 it is seen from the calculated perfusion slopes, that there is reduced perfusion in ROI 3 compared to ROI 1 and ROI 2. This information provides the surgeon with objective perfusion parameters on which to base his surgical decisions and thereby ultimately increase the chance of a successful surgical outcome.

Figure 8A:
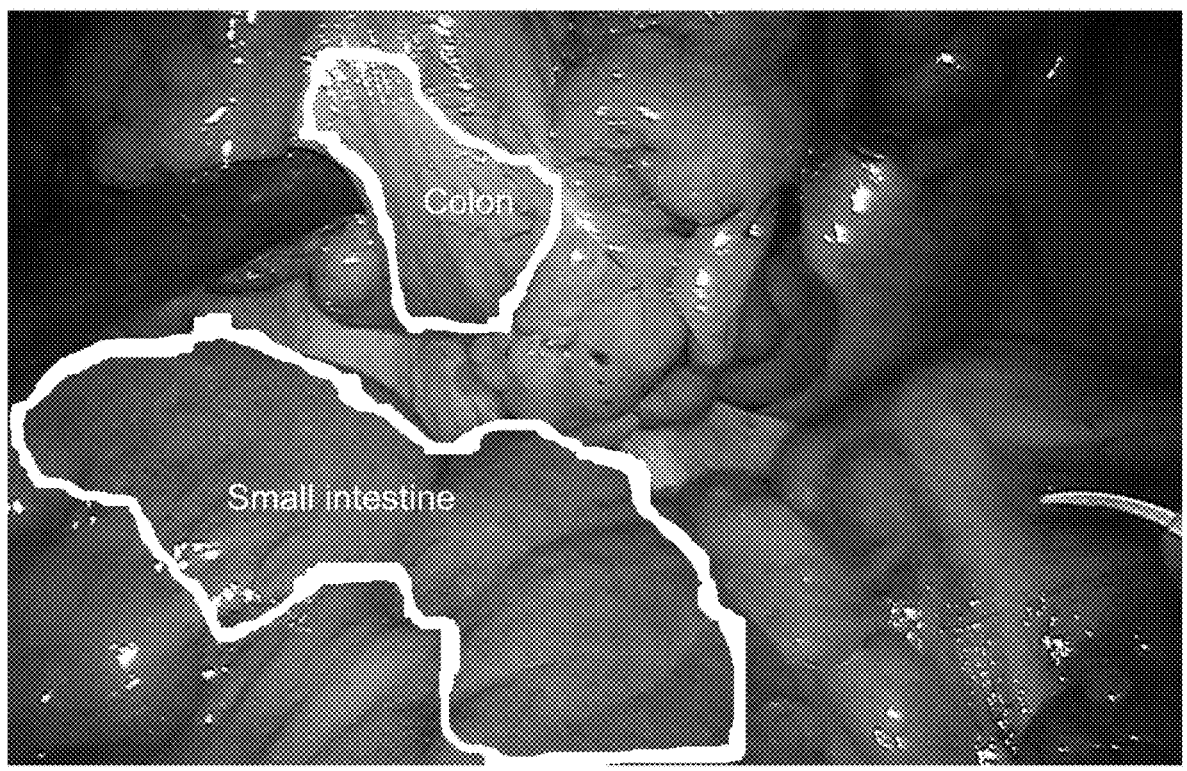
FIG. 8A shows a still image from a normal video sequence acquired before resection of the colon of a patient. The image shows the small intestine (lower part) and the colon (upper part).

FIG. 8A shows a still image from a normal video sequence acquired before resection of the bowel of a patient. The image shows the small intestine (lower part) and the colon (upper part). It is the colon which is about to be resected but by including the small intestine in the image analysis it is possible to provide an additional, possibly unbiased, high-perfusion reference measurement of the perfusion of the patient to be used for comparison with later perfusion measurements.

Figure 8B:
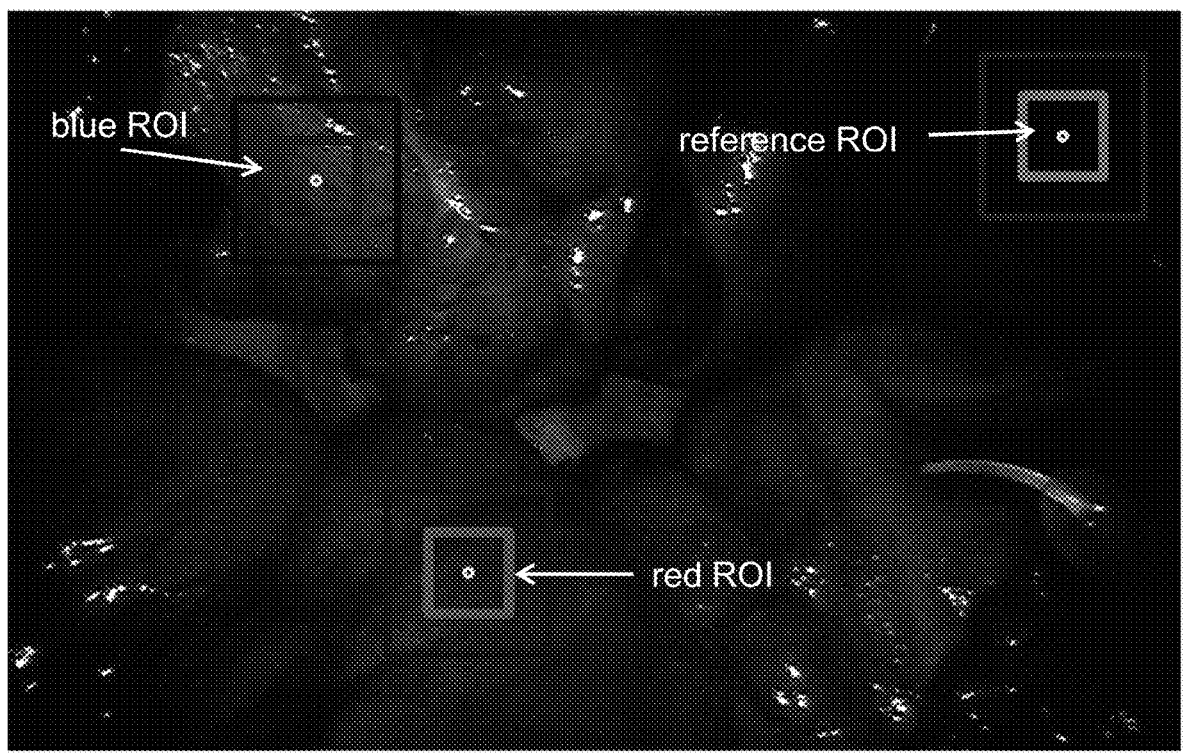
FIG. 8B shows a fluorescent image of substantially the same subsection of the gastrointestinal tract as in FIG. 8A but acquired later, i.e. after a bolus of a fluorescent contrast agent (ICQ) has been injected in the patient.

FIG. 8B shows a fluorescent image of substantially the same subsection of the gastrointestinal tract as in FIG. 8A but acquired later, i.e. after a bolus of a fluorescent contrast agent (ICG) has been injected in the patient. Three ROIs are indicated in the image to be used for image analysis: An upper left blue box located at the colon, a lower red box located at the small intestine (high-perfusion reference) and an upper right box located at a reference position in the image substantially without blood perfusion (no/low-perfusion reference).

Figure 9A:
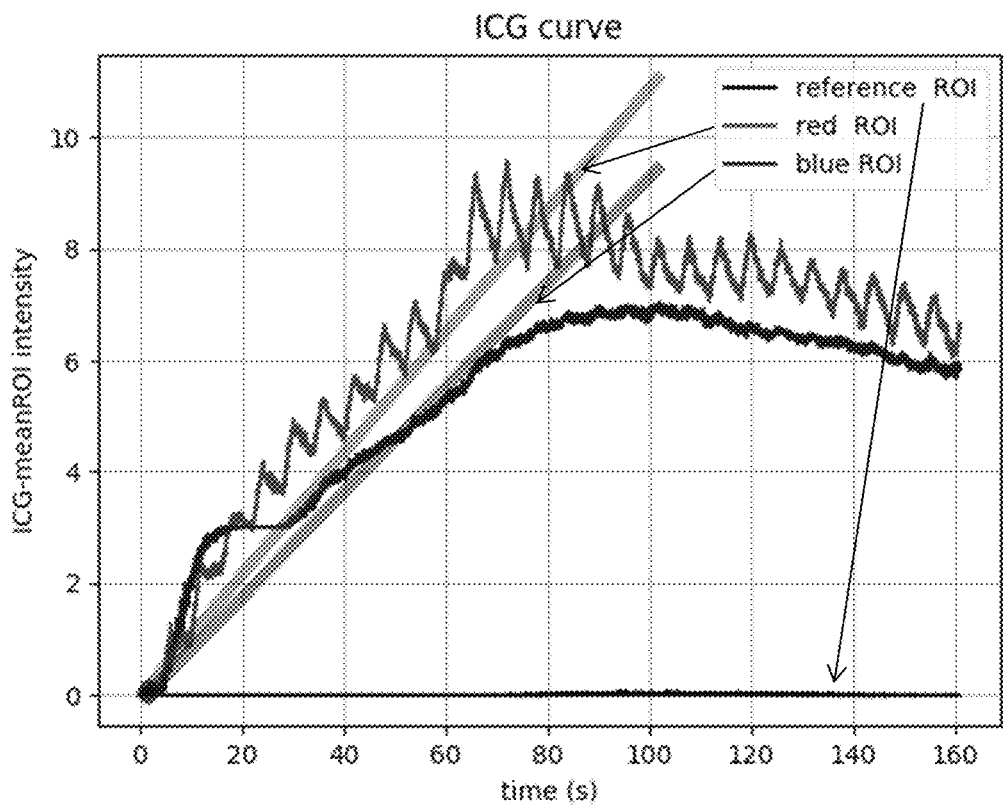
FIG. 9A shows the resulting intensity curves in the ROIs of FIG. 8B and the perfusion slopes calculated according to the herein disclosed approach, i.e. the perfusion slopes of the colon and the small intestine before resection.

FIG. 9A shows the resulting intensity curves in the ROIs of FIG. 8B and the perfusion slopes calculated according to the herein disclosed approach, i.e. the perfusion slopes of the colon and the small intestine before resection. Even though the intensity curves look quite different, the calculated perfusion slopes for the colon and the small intestine are comparable, however, with the perfusion slope of the small intestine being steeper than the perfusion slope of the colon (higher level of perfusion). This is also summarized in FIG. 9B where the perfusion slopes of the small intestine (left) and the colon (right) has been normalized relative to the perfusion slope of the small intestine.

Figure 10A:
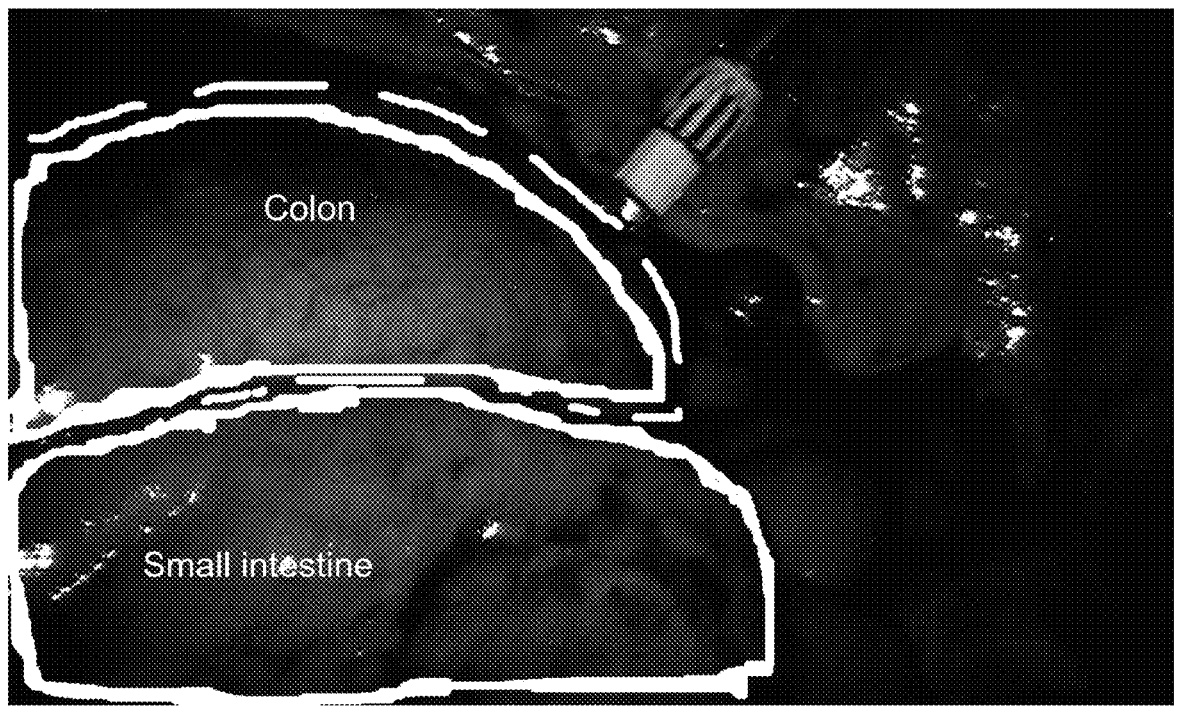
FIG. 10A shows a normal image of substantially the same subsection of the gastrointestinal tract as in FIG. 8A but acquired after resection of the colon—but before anastomosis.

FIG. 10A shows a normal image of substantially the same subsection of the gastrointestinal tract as in FIG. 8A but acquired after resection of the bowel—but before anastomosis. This is a crucial part of the operation where the surgeon must assess whether the perfusion of the two ends of bowel that are left after the resection is adequate for the anastomosis, or whether more of the bowel must be resected to ensure that the anastomosis is created in a region with optimal perfusion, ultimately increasing the chance of a successful outcome. The surgeon is therefore interested in obtaining a measure of the perfusion of various regions of the bowel around the resection. The small intestine is marked in the bottom of the image and the resected bowel (colon) is marked in the top of the image.

Figure 10B:
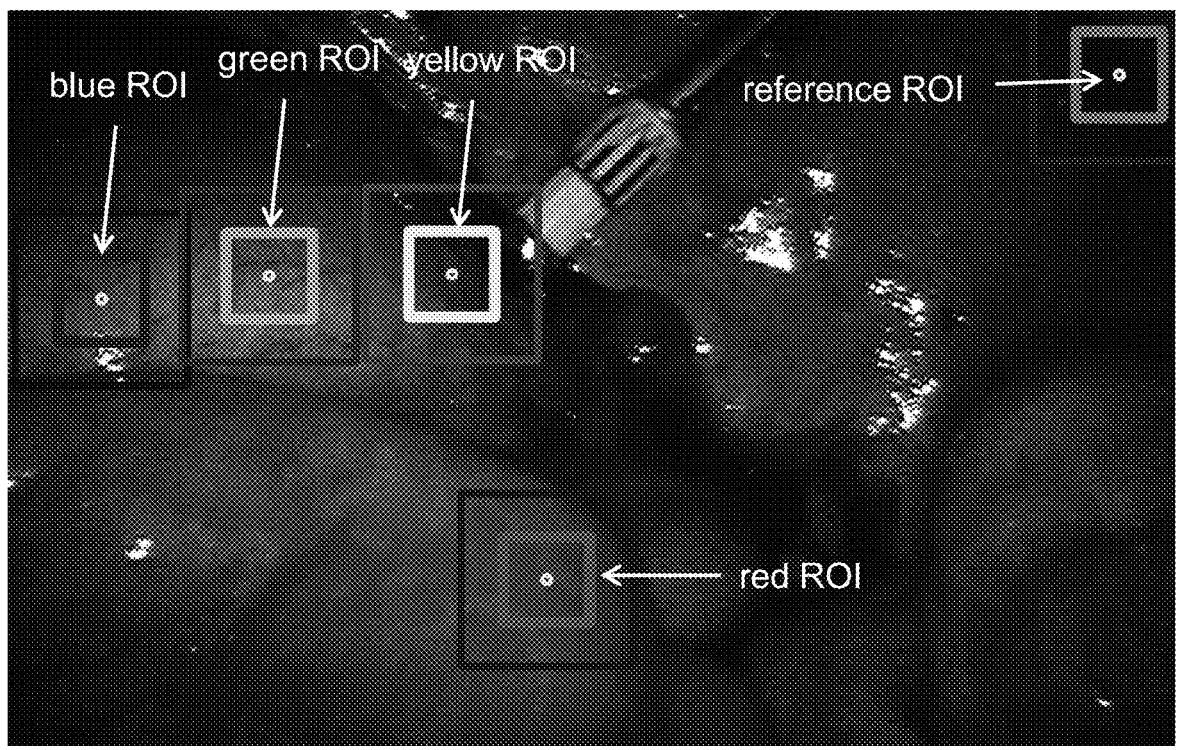
FIG. 10B is a fluorescent image which corresponds to the image in FIG. 10A after a bolus of ICG has been injected. Five ROIs are indicated in the image.

FIG. 10B is a fluorescent image which corresponds to the image in FIG. 10A after a bolus of ICG has been injected. Five ROIs are indicated in the image: One (red) on the small intestine as a high-perfusion reference, one (black) located at a reference position in the image substantially without blood perfusion (no/low-perfusion reference) and three (blue, green and yellow) on the resected bowel (colon).

Figure 9B:
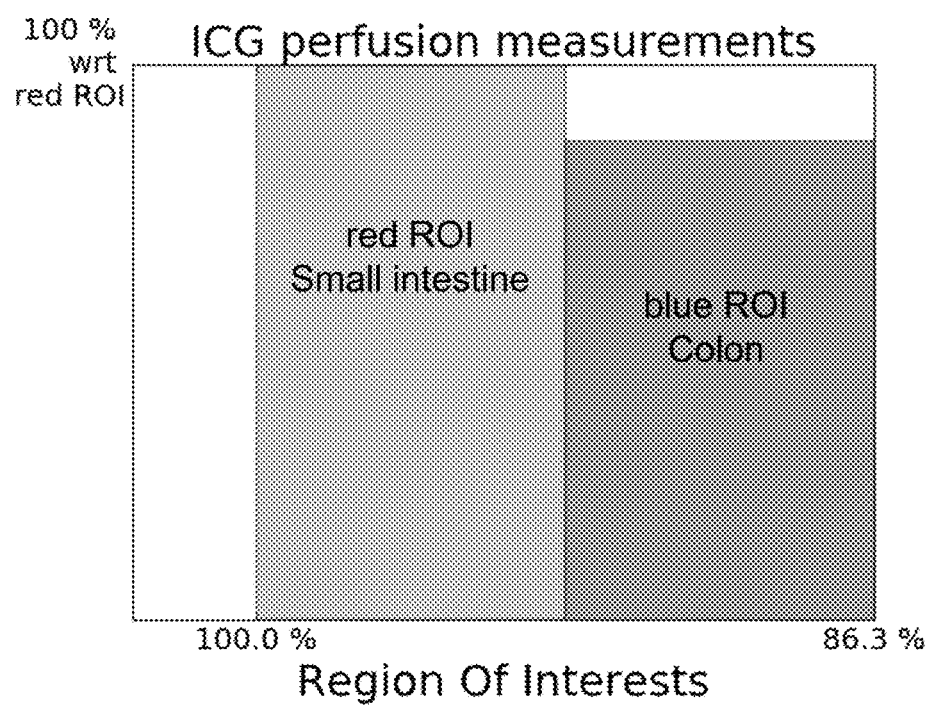
FIG. 9B shows the perfusion slopes of the small intestine (left) and the colon (right) from FIG. 9A, but here in FIG. 9B the slopes have been normalized relative to the perfusion slope of the small intestine.
Figure 11A:
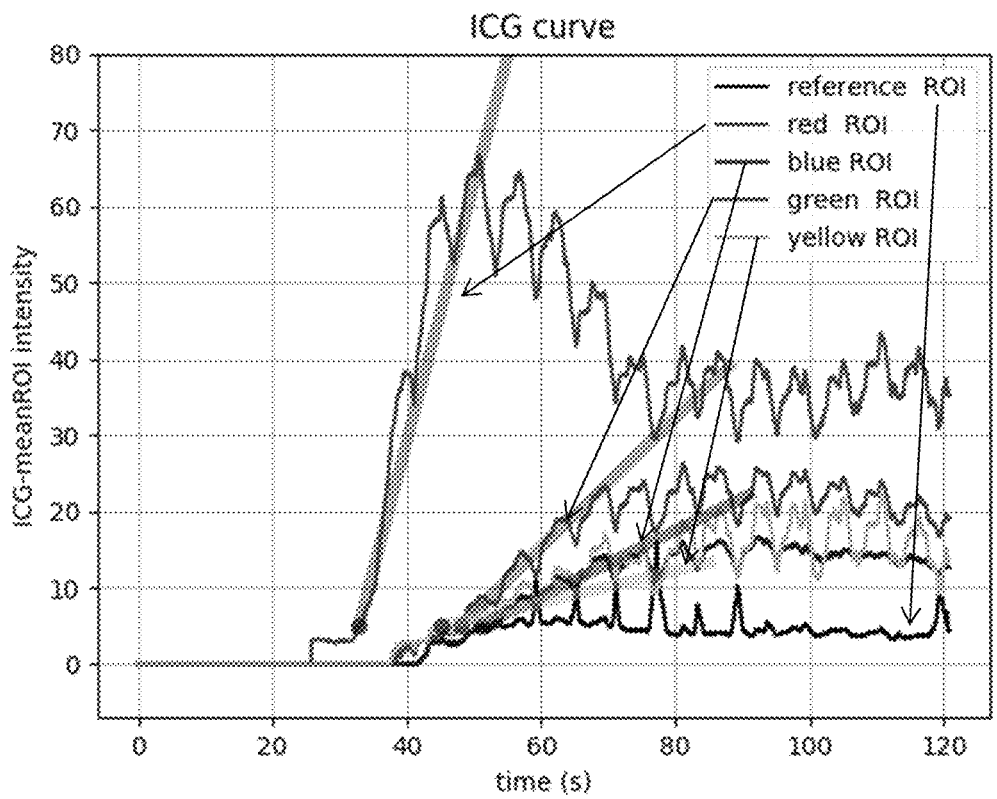
FIG. 11A shows the resulting intensity curves from the measurement illustrated in FIGS. 10A and 10B.
Figure 11B:
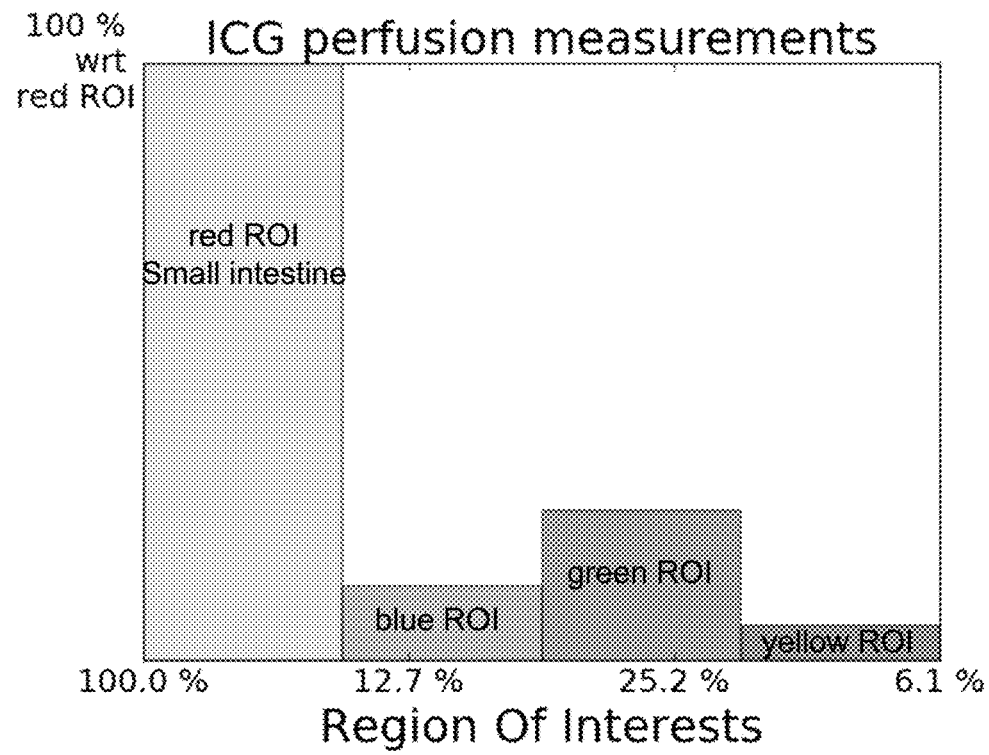
FIG. 11B shows the perfusion slopes of the small intestine (left) and the colon (blue, green and yellow to the right) from FIG. 11A, but here in FIG. 11B the slopes have been normalized relative to the perfusion slope of the small intestine.

FIG. 11A shows the resulting intensity curves from the measurement illustrated in FIGS. 10A and 10B. The red ROI corresponds to the small intestine giving the steepest perfusion slope and the black reference ROI naturally giving the lowest perfusion slope. The blue, green and yellow ROIs. corresponding to the three ROIs which were located on the bowel, provide comparable perfusion slopes, as also summarized in FIG. 11B where the perfusion slopes of the small intestine (left, red) and the bowel (blue, green and yellow to the right) has been normalized relative to the perfusion slope of the small intestine. Comparing to FIG. 9B there is a pronounced difference. In FIG. 9B (before resection) the perfusion in the bowel was comparable to the perfusion in the small intestine, whereas after resection the perfusion in the resected bowel is much lower than the small intestine. It is further noted that when comparing FIG. 9A (before resection) with FIG. 11A (after resection), the perfusion slope in absolute numbers is much larger after resection, also for the small intestine. This indicates that the absolute value of the perfusion slope (and the other perfusion parameters) is less important than a relative value as also demonstrated in FIGS. 9B and 11B. I.e. it is important to have one or more reference ROIs in the image analysis such that the calculated perfusion parameters can be compared to comparable perfusion parameters acquired from the same video footage. In this example, the herein disclosed approach of determining the perfusion detects a marked fall in perfusion of the bowel (colon) relative to the perfusion of the small intestines. This important information can guide the surgeon when choosing the optimal location of the anastomosis.

Figure 12A:
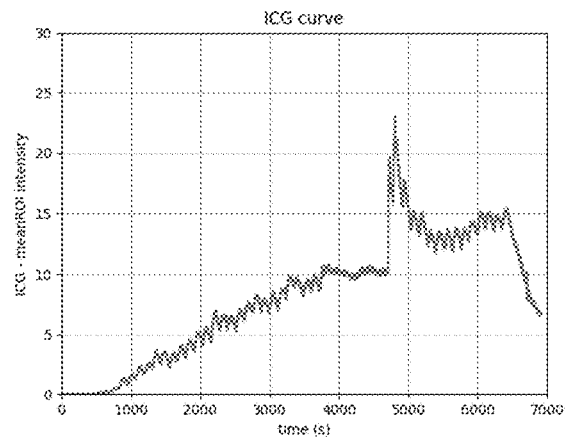
FIG. 12A shows an oscillating time intensity fluorescent curve wherein the oscillations are disrupted due to the onset of ischemia in a human subject.
Figure 12B:
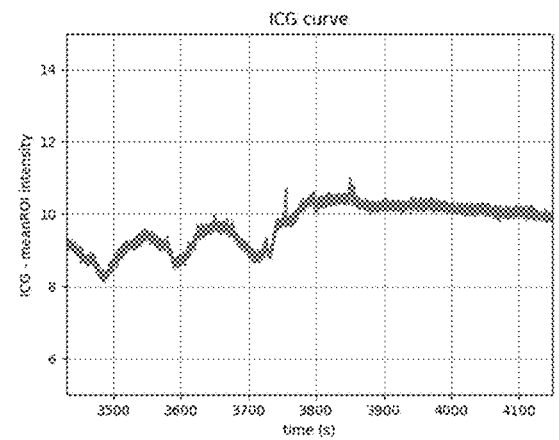
FIG. 12B shows a zoom-in of the time interval around t=3800 s of the previous graph wherein the onset of ischemia occurs.
Figure 12C:
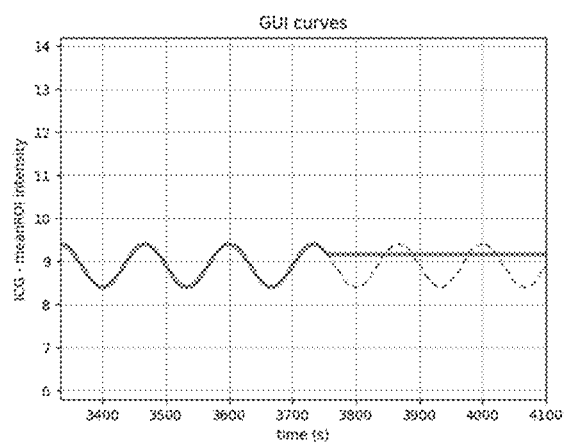
FIG. 12C shows idealized data with and without ischemic conditions.
Figure 12D:
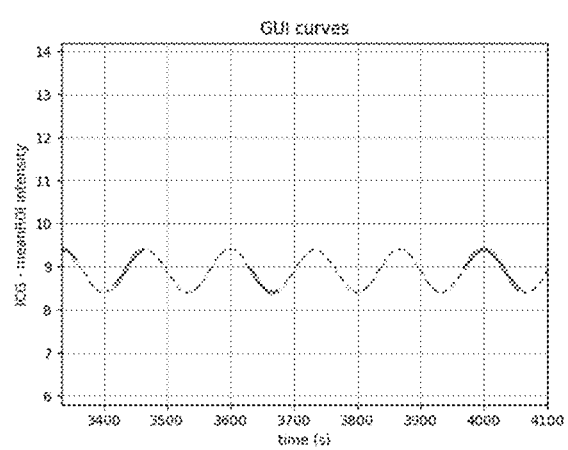
FIG. 12D shows idealized data wherein only parts of the oscillating time intensity fluorescence curve may be detected.

FIG. 12A shows actual measurement data from a human subject. The human subject is repeatably injected with micro boluses of ICG at regular intervals (in this example around 2 minutes). The initial micro bolus of ICG comprised an amount of 0.0046 mg ICG/kg body weight of the human subject and each of the subsequent micro boluses of ICG comprised the same amount of 0.0046 mg ICG/kg body weight of the human subject. The time intensity curve shows a substantially sinusoidal pattern which increases linearly over time. The increase in intensity over time is related to the proportion between the dose of the fluorescent agent and the wash out time, during which the fluorescent intensity decreases. At a certain time point, around t=3800 s, FIG. 12B, the perfusion is restricted causing an onset of ischemia, which can be seen by the lack of oscillations following this time point, forming what can be described as an ischemic flatline.

FIG. 12C shows idealized data displaying a sinusoidal time-intensity curve. The measured ROI intensity increases upon injection of a fluorescence imaging agent and decreases during the wash-out phase. At approximately t=3750 s the measured data shows a stationary measured ROI intensity value due to the onset of ischemic conditions. Alternatively, had there not been ischemic conditions, the measured values are instead expected to follow the dashed line, such that the measured ROI values continuously follows the sinusoidal pattern.

FIG. 12D shows idealized data displaying a sinusoidal time-intensity curve without ischemic conditions wherein the anatomical region of interest drifts in and out of focus. The dashed line shows the expected measurement values if the ROI would be continuously observable. If this is not possible, for example due to the anatomical region of interest drifting in an out of focus of the recorded image, the measured data may not be complete but instead gaps—time intervals wherein no measurement data of the anatomical region of interest have been acquired—may be present. Therefore, the system is preferably able to recognize the sinusoidal pattern even when the recorded data is not complete. If the system is able to correctly recognize the sinusoidal pattern, it is provided with expected intensity values of the ROI at each time point, which thereafter can be used for comparison with measured values. If the measured value(s) differs from the anticipated value(s) the system may be configured to provide the surgeon with an alarm. Therefore, the system may be configured such that it recognizes the phase of the oscillating/sinusoidal pattern of a measured time point or interval, which is thereafter compared to an expected phase of the time point or interval, wherein the expected phase is preferably based on the recognized oscillating pattern and/or the known frequency of the repeated bolus injections. As a result, the system does not necessarily require continuous measurement values, but may instead be based on the expected phase of the oscillating pattern in combination with the time information of the measured time point or interval, such that a specific phase of the oscillating pattern is expected to be present in the measured interval.

Figure 13A:
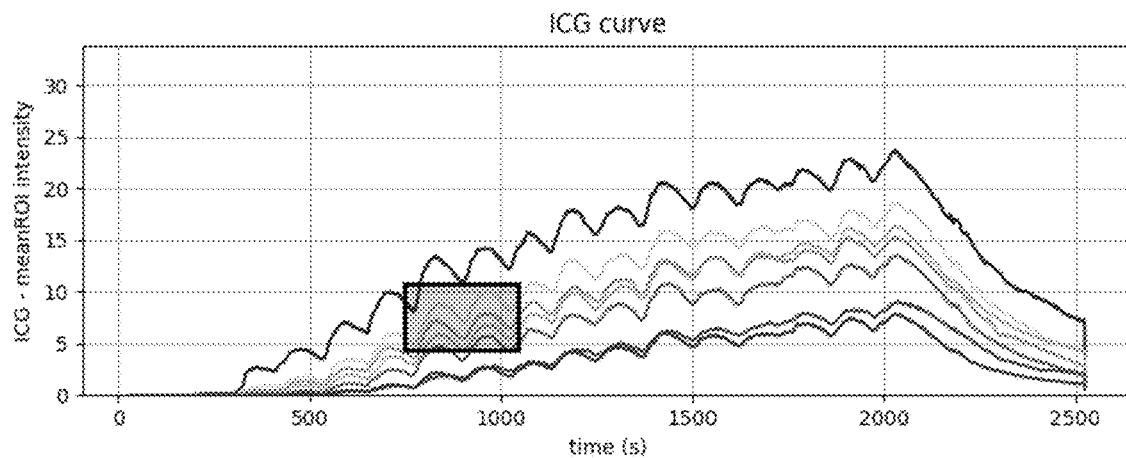
FIG. 13A shows continuous measurements of a human subject injected with micro boluses.

FIG. 13A shows a fluorescent intensity measurement of a human subject conducted over a longer time interval, approximately 40 minutes, wherein the human subject has been repeatedly injected with micro boluses of ICG. The initial micro bolus of ICG comprised an amount of 0.0058 mg ICG/kg body weight of the human subject and each of the subsequent micro boluses of ICG comprised the same amount of 0.0058 mg ICG/kg body weight of the human subject. The intensities of seven separate ROIs where measured, and have been assigned separate colours in the graph. The measured fluorescence intensities show cyclic sinusoidal patterns wherein the frequencies agree with the injection frequency (around 120 s). The patterns are substantially linearly increasing due to the accumulation of the fluorescence imaging agent, due to the relatively short period of the injections in comparison to the dose size. At approximately t=2000 s, the repeated injections of the fluorescence imaging agent are stopped causing an approximately exponential decay of the fluorescence intensity.

Figure 13B:
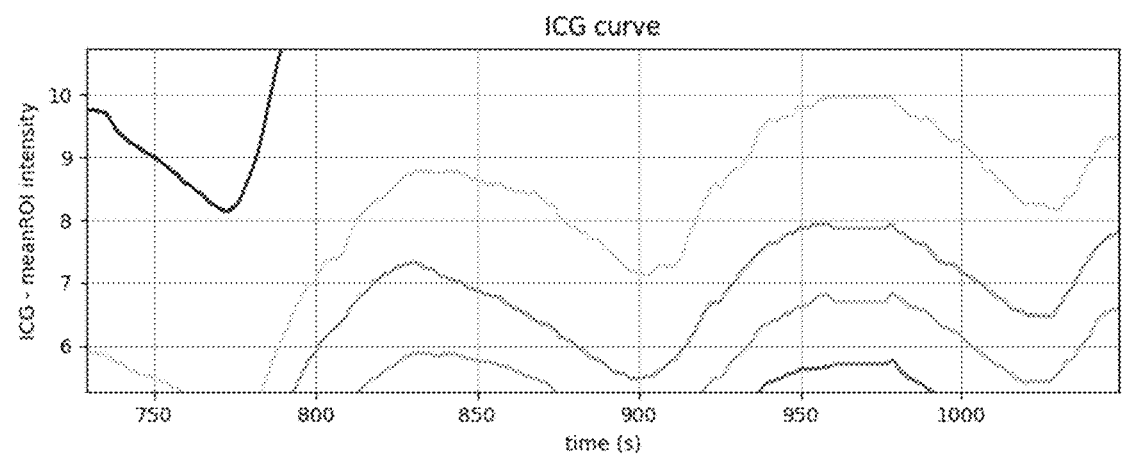
FIG. 13B shows a zoom-in of the interval indicated in FIG. 13A.
Figure 13C:
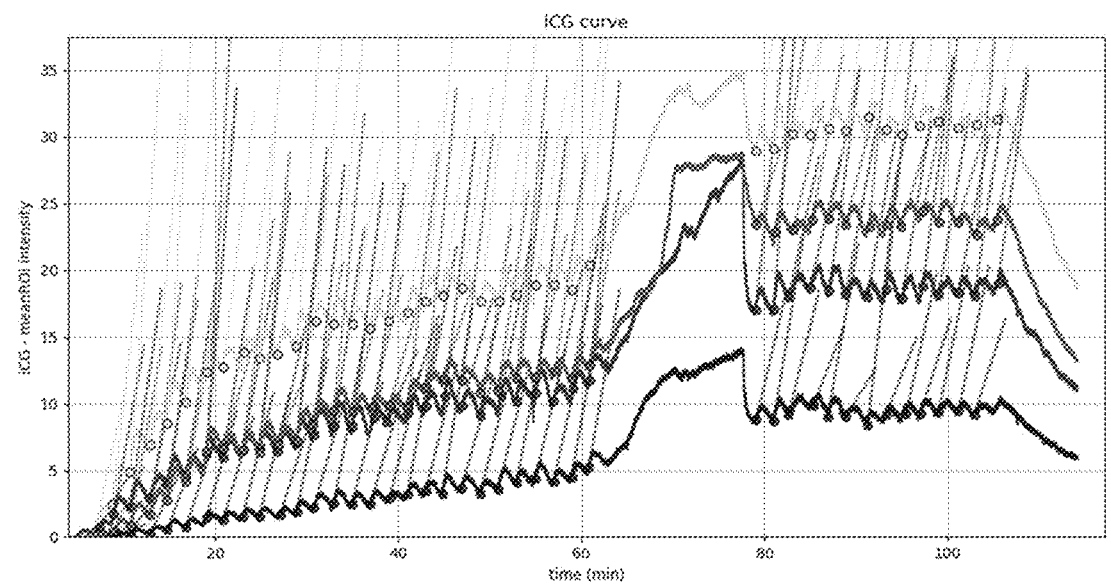
FIG. 13C shows measurements of a human, subjected to venous occlusion, wherein the blood flow is only partially restricted.

FIG. 13B shows a zoom-in of the marked region in FIG. 13A. Here, the smaller fluctuations within the same ROI as well as between different ROIs can be seen. At the same time, the cyclic intensity patterns are distinct with the pattern of each ROI have an identical period.

FIG. 13C shows time-intensity plots of a measurement carried out on a human subject by repeatable injections of micro boluses of the fluorescence imaging agent. The initial micro bolus of ICG comprised an amount of 0.0046 mg ICG/kg body weight of the human subject and each of the subsequent micro boluses of ICG comprised the same amount of 0.0046 mg ICG/kg body weight of the human subject. The graph shows the result of a venous occlusion wherein, between approximately t=62-78 minutes, the perfusion is restricted, while not completely hindered. In this case, the oscillating dynamics of the measured fluorescence intensities ceases and the measurements display an irregular increase during the venous occlusion. Therefore, it should be noted that decreased perfusion does not necessarily result in a flatline, as is otherwise typically the result during ischemic conditions.

REFERENCES

[1] C. Toens et al: Validation of IC-VIEW fluorescence videography in a rabbit model of mesentereic ischaemia and reperfusion. Int J Colorectal Dis 2006; 21:332-338.
[2] N. Nerup et al: Quantification of fluorescence angiography in a porcine model. Langenbecks Arch Surg, published online 15 Nov. 2016.
[3] L. Boni et al: Indocyanine green-enhanced fluorescence to assess bowel perfusion during laparoscopic colorectal resection. Surg Endosc (2016) 30:2736-2742
[4] R. Uitert et al: A stable optic-flow based method for tracking colonoscopy images. Conference Paper, July 2008
[5] US 2016/262638

[6] D. Stein et al.: Colon Resection. http://emedicine.medscape.com/article/1891505-overview, September 2015

Items
1. A method of automatic perfusion assessment of an anatomical structure of a subject, the method comprising administration into a vein of a bolus corresponding to less than 0.01 mg ICG/kg body weight of a first fluorescence imaging agent, acquiring and analysing a time series of fluorescence images of the tissue of said anatomical structure following the injection of the first fluorescence imaging agent, and determining at least one perfusion parameter of said anatomical structure based on said analysis.
2. The method of item 1, wherein the agent is injected by a controllable injection pump.
3. The method of any of the preceding items, wherein the agent is injected as a series of boluses with a predefined time between subsequent boluses.
4. The method of any of the preceding items, wherein the fluorescence emission from the anatomical structure is measured following injection of each bolus.
5. The method of any of the preceding items, wherein the bolus comprises incrementally increasing or incrementally decreasing amounts of the agent.
6. The method of item 5, wherein the amount increases or decreases in increments of 10% from one bolus to the subsequent bolus.
7. The method of any of the preceding items, wherein the minimum bolus that provides a quantifiable fluorescence emission representative of the perfusion of the anatomical structure is determined following administering a series of increasing or decreasing boluses.
8. The method of any of the preceding items, wherein the interval between boluses is between 5 and 600 seconds, such as between 15 and 300 seconds, for example between 45 and 210 seconds, such as between 90 and 120 seconds.
9. The method of any of the preceding items, wherein the interval between boluses is sufficiently long to allow measurement of a perfusion slope for each bolus in the anatomical structure, preferably wherein the perfusion slope includes a slope start and a washout slope.
10. The method of any of the preceding items, wherein a volume of isotonic solution (such as saline) is injected immediately following injection of a bolus of fluorescence imaging agent, for example wherein the volume is 1-20 mL, such as 2.5-15 mL, for example 5-10 mL.
11. The method of any of the preceding items, wherein the amount of fluorescence imaging agent corresponds to between 0.0001 and 0.01 mg ICG/kg body weight per bolus, such as between 0.0001 and 0.01 mg ICG/kg body weight per bolus.
12. The method of any of the preceding items, wherein an initial amount of fluorescence imaging agent corresponds to at least 0.001 mg ICG/kg body weight.
13. The method of item 12, wherein subsequent boluses increase or decrease corresponding to at least 0.001 mg ICG/kg body weight from one bolus to the subsequent.
14. The method of any of the preceding items, wherein the bolus is a liquid volume between 0.5 µL and 10 mL, such as from 0.5-5 mL.
15. The method of any of the preceding items, wherein a second fluorescence imaging agent is administered, the second fluorescence imaging agent having an emission maximum differing from the emission maximum of the first fluorescence imaging agent by at least 50 nm.
16. The method of any of the preceding items, wherein a third, a fourth, a fifth or further fluorescence imaging agents are administered.
17. The method of item 15 or 16, wherein the first and subsequent fluorescence imaging agents are administered alternatingly.
18. The method of items 15, 16 or 17, wherein the interval between administrations of different fluorescence imaging agents is half of the interval between subsequent administrations of the same fluorescence imaging agent.
19. The method of any of the preceding items, wherein the fluorescence is detected automatically by illuminating the anatomical structure with a light source capable of exciting the fluorescence imaging agent, and the emission is quantified through a series of fluorescence images of the anatomical structure.
20. The method of any of the preceding items, wherein the period between boluses is determined by a computer configured to detect the perfusion slope caused by each bolus.
21. The method of any of the preceding items, wherein the dose of the fluorescence imaging agent and/or the period between boluses are chosen such that an oscillating pattern of the time series of the mean intensity of the ROI can be received.
22. The method of any of the preceding items, wherein a longer pause, such as at least 1 minute, between boluses is held at regular intervals, such as every 20 bolus, more preferably every 40 bolus, most preferably every 60 bolus, such that the background fluorescence level can be reduced.
23. The method of any of the preceding items, wherein the amount of fluorescence imaging agent in a bolus is controlled by a computer configured to determine a minimum bolus capable of determining a minimum fluorescence emission representative of the perfusion of the anatomical structure.
24. The method according to any of the preceding items, wherein the anatomical structure is the gastrointestinal tract, preferably including buccal cavity; pharynx; the small intestine including duodenum, jejunum, and ileum; the stomach, including esophagus, cardia, and pylorus; the large intestine including cecum, colon, rectum and the anal canal.
25. The method according to any of the preceding items, wherein the anatomical structure is an internal organ of the subject.
26. The method according to any of the preceding items, wherein the anatomical structure is the skin of the subject.
27. The method according to any of the preceding items, wherein the anatomical structure comprises a wound which is the subject of the perfusion assessment.
28. The method according to any of the preceding items, wherein the fluorescence imaging agent comprises indocyanine green (ICG), fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof
29. The method according to any of preceding items, further comprising the step of tracking movements of the anatomical structure in said video images.

30. The method according to any of preceding items, further comprising the step of tracking movements of at least a part of the anatomical structure in said video images, and correlating said movements such that at least said first region of interest corresponds to the same subsection of the anatomical structure in said video images.
31. The method according to any of preceding items, wherein movement tracking is provided by free image tracking.
32. The method according to any of preceding items, wherein movement tracking is provided by free image tracking in the form of classifier based tracking comprising the step of determining classifiers of one more recognizable features in the video images, preferably in an area adjacent or surrounding at least one of the regions of interest.
33. The method according to any of preceding items, wherein movement tracking is provided by free image tracking in the form of colour based tracking.
34. The method according to any of preceding item, wherein movement tracking is based on colour tracking of one or more colour markers which have been applied on to the gastrointestinal tract.
35. The method according to any of preceding items, wherein movement tracking comprises the step of colour filtering and thresholding to obtain a Boolean map of pixels in the video images.
36. The method according to any of preceding items, further comprising the step of noise filtering to improve the Boolean map.
37. The method according to any of preceding items, wherein movement tracking is provided by object based tracking.
38. The method according to any of preceding items, wherein movement tracking is provided by tracking the movement of one or more predefined objects attached to the anatomical structure.
39. The method according to any of preceding items, comprising the step of creating ROI templates by initially storing an image of each ROI, and wherein movement tracking is provided by applying cross-correlation to each ROI template.
40. The method according to any of preceding items, wherein the tracking is carried out such that three-dimensional information of the at least a part of an anatomical structure is acquired.
41. The method according to any of the preceding items, wherein the perfusion assessment comprises localizing a perfusion complication in the anatomical structure.
42. The method according to any of the preceding items, wherein the perfusion assessment is used in connection with a diagnostic or surgical procedure.
43. The method according to item 42, wherein the procedure comprises diagnostic laparoscopy, explorative laparoscopy, surgical laparoscopy with traditional laparoscopy, robotic surgery, and open surgery.
44. The method according to item 42, wherein the procedure comprises anastomosis, such as intestinal anastomosis.
45. A fluorescence imaging agent for use in a method according to any of the preceding items.
46. Use of a fluorescence imaging agent in the preparation of a medicament for use in a method of automatic perfusion assessment according to any of the preceding items 1-44.
47. A system for automatic perfusion assessment of an anatomical structure during a medical procedure of a subject comprising a controllable injection pump for holding at least one first fluorescence imaging agent, the injection pump being configured for injecting a predefined amount of said first fluorescence imaging agent into the blood of the subject, wherein the system is configured for receiving and analysing a time series of fluorescence images of the tissue of said anatomical structure following the injection of the first fluorescence imaging agent, and determining at least one perfusion parameter of said anatomical structure based on said analysis.
48. The system according to any of the preceding items, wherein the system is configured to control the injection pump to inject an initial small bolus of fluorescence imaging agent, preferably an amount corresponding to less than 0.01 mg ICG/kg body weight, and subsequently analyse the fluorescence emission resulting from the initial bolus.
49. The system according to any of the preceding items, wherein the system is configured to control the injection pump to inject an initial small bolus of fluorescence imaging agent, preferably an amount corresponding to less than 1 mg ICG or less than 0.8 mg ICG, or less than 0.6 mg ICG, or less than 0.4 mg ICG, or less than 0.2 mg ICG, and subsequently analyse the fluorescence emission resulting from the initial bolus.
50. The system according to any of the preceding items, wherein the system is configured to determine a subject specific minimum effective bolus of fluorescence imaging agent by:
    controlling the injection pump to inject a series of boluses with predefined incrementally increasing or incrementally decreasing amounts of fluorescence imaging agent with a predefined time period between each bolus,
    analyse the fluorescence emission from the anatomical structure following the injection of each bolus, and
    determine the size of the minimum bolus that provides a quantifiable fluorescence emission from the anatomical structure.
51. The system according to any of the preceding items, wherein the system is configured for 1) receiving a time series of images of the tissue of said anatomical structure prior to injection of the fluorescence agent, and 2) determining the background noise level therefrom.
52. The system according to any of the preceding items, wherein the system is configured to determine the subject specific conversion period defined as the time period from injection of a bolus of the fluorescence imaging agent to a rise of a fluorescence slope in the fluorescence emission.
53. The system according to any of the preceding items, wherein the system is configured to determine the subject specific disruption interval defined as the time period from the rise of a fluorescence slope to the fluorescence emission equals the background noise.
54. The system according to any of the preceding items, wherein the system is configured to automatically 1) control the injection pump to inject a series of predefined boluses of fluorescence imaging agent, a predefined bolus such as the minimum effective bolus, with a predefined duration between each bolus, and 2) determine at least one perfusion parameter of said anatomical structure following the injection of each bolus.

55. The system according to any of the preceding items, wherein the system is configured for determining said at least one perfusion parameter in one or more regions of interest located in said anatomical structure and optionally in neighbouring anatomical structures.
56. The system according to any of the preceding items, wherein the system is configured to automatically 1) control the injection pump to inject a series of boluses with incrementally increasing or incrementally decreasing amounts of fluorescence imaging agent with a predefined time period between each bolus, and 2) determine at least one perfusion parameter of said anatomical structure following the injection of each bolus.
57. The system according to any of the preceding items, comprising at least a second controllable injection pump for holding at least a second fluorescence agent which is different from the first fluorescent agent, the second injection pump being configured for injecting a predefined amount of said second fluorescence imaging agent into the blood of the subject.
58. The system according to any of the preceding items, wherein the system is configured for determining said at least one perfusion parameter in one or more regions of interest located in said anatomical structure and optionally in neighbouring anatomical structures.
59. The system according to any of the preceding items 58, configured such that said regions of interest can be selected by a user of the system.
60. The system according to any of the preceding items, further comprising at least one light source configured to provide excitation light to induce fluorescence emission from said first and/or second fluorescent agent in said anatomical structure.
61. The system according to any of the preceding items, further comprising an imaging unit configured for recording at least one time series of the fluorescence emission from the anatomical structure.
62. The system according to any of the preceding items, wherein the imaging unit is configured for white light imaging.
63. The system according to any of the preceding items, configured for forwarding said at least one perfusion parameter for presentation on a display.
64. The system according to any of the preceding items, wherein the anatomical structure is the gastrointestinal tract, preferably including buccal cavity; pharynx; the small intestine including duodenum, jejunum, and ileum; the stomach, including esophagus, cardia, and pylorus; the large intestine including cecum, colon, rectum and the anal canal.
65. The system according to any of the preceding items, wherein the anatomical structure is an internal organ of the subject.
66. The system according to any of the preceding items, wherein the anatomical structure is the skin of the subject.
67. The system according to any of the preceding items, wherein the anatomical structure comprises a wound which is the subject of the perfusion assessment.
68. The system according to any of the preceding items, wherein the system is part of laparoscopic setup wherein the imaging unit and light source are incorporated in laparoscopic units.
69. The system according to any of the preceding items, wherein the system is part of an Open Surgery setup wherein the imaging unit and light source are incorporated in an Open Surgery surgical unit.
70. The system according to any of the preceding items, wherein the fluorescence imaging agent comprises indocyanine green (ICG), fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof
71. The system according to any of the preceding items, wherein the system is configured for assessing the drainage area of a vein or a group of veins, lymph vessels, lymph nodes or other parts of the circulatory and/or lymphatic pathways.
72. The system according to any of the preceding items, configured to carry out the method of any of items 1-44.
73. A computer-implemented method for detecting perfusion changes of at least a part of an anatomical structure, wherein repeatable boluses, comprising a fluorescence imaging agent, are continuously injected to the subject; the method comprising the steps of:
    i. measuring a time series of fluorescence intensity of a region of interest of at least a part of an anatomical structure;
    ii. recognizing a measured pattern of the measured time series,
    iii. creating an expected pattern, based on the measured pattern, which the fluorescence intensity of at least a part of the anatomical region of interest is expected to follow;
    iv. measuring fluorescence intensity of the anatomical region of interest;
    v. analyzing discrepancies between the expected pattern and measured values; and
    vi. repeating steps iv. and v. to continuously assess the perfusion of the at least a part of the anatomical region of interest.
74. The computer-implemented method of item 73, wherein a user is alerted based on differences between the expected pattern and measured values according to a predetermined function, such as a predetermined threshold.
75. The computer-implemented method of any of item 73-74, wherein the recognized oscillating pattern is continuously updated between step iv. and v.
76. The computer-implemented method of any of item 73-75, wherein the oscillating pattern is recognized based on the frequency, the amplitude, the phase and/or the background intensity.
77. The computer-implemented method of any of item 73-76, wherein the boluses are substantially the minimum effective bolus.
78. The computer-implemented method of any of item 73-77, wherein injection parameters, such as the injection frequency, is additionally or alternatively used for recognizing the oscillating pattern.
79. The computer-implemented method of any of item 73-78, wherein the method is used for predicting the onset of ischemic conditions.
80. The computer-implemented method of any of item 73-79, wherein the anatomical region of interest is detected by tracking.

81. The computer-implemented method of any of item 73-80, wherein tracking of the anatomical region of interest is carried out in three dimensions.
82. The computer-implemented method of any of item 73-81, wherein the boluses are injected with a longer phase, such as between 1 and 5 minutes, more preferably between 1 and 4 minutes, even more preferably between 1 and 3 minutes, most preferably between 1.5 and 2.5 minutes.
83. The computer-implemented method of any of item 73-82, wherein a longer pause, such as between 1-10 minutes, wherein no fluorescent imaging agent is injected into the subject is carried out periodically, such as after every 10-300 bolus, more preferably after every 30-300 bolus, more preferably after every 90-300 bolus, most preferably after every 200-300 bolus.
84. The computer-implemented method of any of item 73-83, wherein the user is alerted based on differences between the measured values and expected values in terms of the phase, the frequency and/or the amplitude.
85. The computer-implemented method of any of item 73-84, wherein the method is able to detect ischemia and/or venous occlusion and/or assessing the perfusion area of an artery.
86. The computer-implemented method of any of item 73-85, wherein the method is configured to compensate for measurements of non-continuous intervals, such as when the region of interest drifts in and out of focus, and compare these to the expected pattern.
87. A computer implemented method for detecting perfusion changes of an anatomical region of interest of a subject by image processing hemodynamics in at least a part of said anatomical region of interest in video images acquired from the subject, the method comprising the steps of:
    performing image analysis of at least one video sequence acquired during and/or after a plurality of boluses comprising fluorescence imaging agent are supplied to the subject, wherein the plurality of boluses are supplied according to a predefined pattern, such as in terms of frequency and/or dose,
    calculating subsequent perfusion parameters in one or more regions of interest based on the image analysis, and
    monitoring the subsequent perfusion parameters to determine a change in perfusion in said region(s) of interest.
88. The method of item 87 comprising the steps of any of items 1-46 or items 73-86.
89. A system for automatic perfusion assessment of an anatomical structure during a medical procedure of a subject, the system comprising a controllable injection pump for holding at least one first fluorescence imaging agent, the injection pump being configured for injecting a bolus corresponding to a predefined amount of said first fluorescence imaging agent into a vein of the subject, wherein the system is configured for receiving and analysing a time series of fluorescence images of the tissue of said anatomical structure following the injection of the first fluorescence imaging agent, and determining at least one perfusion parameter of said anatomical structure based on said analysis.
90. The system according to item 89, wherein the bolus corresponds to less than 0.01 mg ICG/kg body weight of the first fluorescence imaging agent.
91. The system according to item 89, wherein the bolus corresponds to less than 0.5 mg ICG of the first fluorescence imaging agent.
92. The system according to item 89, wherein the fluorescence agent is ICG and wherein the amount of ICG in the bolus is less than 0.01 mg/kg body weight.
93. The system according to item 89, wherein the fluorescence agent is ICG and wherein the amount of ICG in the bolus is less than 1 mg ICG or less than 0.5 mg ICG.
94. The system according to any of the preceding items, wherein the system is configures to inject boluses with an interval between 5 and 600 seconds, such as between 15 and 300 seconds, for example between 45 and 210 seconds, such as between 90 and 120 seconds.
95. The system according to any of the preceding items, wherein the system is configured to determine a subject specific minimum effective bolus of fluorescence imaging agent by:
    controlling the injection pump to inject a series of boluses with varying amounts of fluorescence imaging agent with a predefined time period between each bolus,
    analyse the fluorescence emission from the anatomical structure following the injection of each bolus, and
    determine the size of the minimum bolus that provides a quantifiable fluorescence emission from the anatomical structure.
96. The system according to item 95, wherein a quantifiable fluorescence emission from the anatomical structure corresponds to a fluorescence emission such that a perfusion slope can be determined.
97. The system according to any of the preceding items, wherein the system is configured to determine the subject specific disruption interval defined as the time period from the rise of a fluorescence slope to the fluorescence emission falls below a number of standard deviations, such as 20, 10 or 5 standard deviations, from a background noise.
98. The system according to any of the preceding items, wherein the system is configured to automatically 1) control the injection pump to inject a series of predefined boluses of fluorescence imaging agent, a predefined bolus such as the minimum effective bolus, with a predefined duration between each bolus, and 2) determine at least one perfusion parameter of said anatomical structure following the injection of each bolus.
99. The system according to any of the preceding items, wherein the system is configured to automatically 1) control the injection pump to inject a series of boluses with varying amounts of fluorescence imaging agent with a predefined time period between each bolus, and 2) determine at least one perfusion parameter of said anatomical structure following the injection of each bolus.
100. The system according to any of the preceding items, configured for holding at least a second fluorescence agent which is different from the first fluorescent agent, and wherein the system is configured for injecting one or more boluses having a predefined amount of said second fluorescence imaging agent into the blood of the subject.
101. The system according to any of the preceding items, wherein the system is configured for determining said at least one perfusion parameter in one or more regions of interest located in said anatomical structure and optionally in neighbouring anatomical structures, and wherein said regions of interest optionally can be selected by a user of the system.

102. The system according to any of the preceding items, further comprising at least one light source configured to provide excitation light to induce fluorescence emission from said first and/or second fluorescent agent in said anatomical structure, and an imaging unit configured for recording at said time series of the fluorescence emission from the anatomical structure.

103. The system according to any of the preceding items, further configured for tracking movements of at least a subsection of the anatomical structure in said time series of images, and correlating said movements such that at least said first region of interest corresponds to the same subsection of the anatomical structure in said images and wherein movement tracking is provided by free image tracking and/or by object based tracking.

104. A method of automatic perfusion assessment of an anatomical structure of a subject, the method comprising administration into a vein of a bolus corresponding to less than 0.01 mg ICG/kg body weight of a first fluorescence imaging agent, acquiring and analysing a time series of fluorescence images of the tissue of said anatomical structure following the injection of the first fluorescence imaging agent, and determining at least one perfusion parameter of said anatomical structure based on said analysis.

105. The method of item 104, wherein the agent is injected by a controllable injection pump.

106. The method of any of the preceding items 104-105, wherein the agent is injected as a series of boluses with a predefined time between subsequent boluses.

107. The method of any of the preceding items 104-106, wherein the fluorescence emission from the anatomical structure is measured following injection of each bolus.

108. The method of any of the preceding items 104-107, wherein the bolus comprises incrementally increasing or incrementally decreasing amounts of the agent.

109. The method of item 108, wherein the amount increases or decreases in increments of 10% from one bolus to the subsequent bolus.

110. The method of any of the preceding items 104-109, wherein the minimum bolus that provides a quantifiable fluorescence emission representative of the perfusion of the anatomical structure is determined following administering a series of increasing or decreasing boluses.

111. The method of any of the preceding items 104-110, wherein the interval between boluses is between 5 and 600 seconds, such as between 15 and 300 seconds, for example between 45 and 210 seconds, such as between 90 and 120 seconds.

112. The method of any of the preceding items 104-111, wherein the interval between boluses is sufficiently long to allow measurement of a perfusion slope for each bolus in the anatomical structure, preferably wherein the perfusion slope includes a slope start and a washout slope.

113. The method of any of the preceding items 104-112, wherein a volume of isotonic solution (such as saline) is injected immediately following injection of a bolus of fluorescence imaging agent, for example wherein the volume is 1-20 mL, such as 2.5-15 mL, for example 5-10 mL.

114. The method of any of the preceding items 104-113, wherein the amount of fluorescence imaging agent corresponds to between 0.001 and 0.01 mg ICG/kg body weight per bolus, such as between 0.001 and 0.01 mg ICG/kg body weight per bolus.

115. The method of any of the preceding items 104-114, wherein an initial amount of fluorescence imaging agent corresponds to at least 0.001 mg ICG/kg body weight.

116. The method of item 115, wherein subsequent boluses increase or decrease corresponding to at least 0.001 mg ICG/kg body weight from one bolus to the subsequent.

117. The method of any of the preceding items 104-116, wherein the bolus is a liquid volume between 0.5 μL and 10 mL, such as from 0.5-5 mL.

118. The method of any of the preceding items 104-117, wherein a second fluorescence imaging agent is administered, the second fluorescence imaging agent having an emission maximum differing from the emission maximum of the first fluorescence imaging agent by at least 50 nm.

119. A computer implemented method for detecting perfusion changes of an anatomical region of interest of a subject by image processing hemodynamics in at least a part of said anatomical region of interest in video images acquired from the subject, the method comprising the steps of:
performing image analysis of at least one video sequence acquired during and/or after a plurality of boluses comprising fluorescence imaging agent are supplied to the subject, wherein the plurality of boluses are supplied according to a predefined pattern, such as in terms of frequency and/or dose,
calculating subsequent perfusion parameters in one or more regions of interest based on the image analysis, and
monitoring the subsequent perfusion parameters to determine a change in perfusion in said region(s) of interest.

120. The method of item 119 comprising the steps of any of items 104-118.

The invention claimed is:

1. A method of automatic blood perfusion assessment of a tissue of an anatomical structure of a subject, the method comprising:
administering a first fluorescence imaging agent having an emission maximum into a vein of the subject as a first bolus and a series of subsequent boluses with a predefined time between the subsequent boluses, the first bolus, and each subsequent bolus, comprising an amount of the first fluorescence imaging agent corresponding to less than 0.005 mg ICG/kg body weight of the subject, wherein the amount of the first fluorescence imaging agent is dissolved in a liquid;
acquiring and analysing a time series of fluorescence images of the tissue of said anatomical structure following administering the first bolus of the first fluorescence imaging agent, producing an analysis based on a fluorescence intensity in said images; and
determining at least one blood perfusion parameter of said anatomical structure based on said analysis.

2. The method of claim 1, wherein the first bolus comprises an amount of the first fluorescence imaging agent corresponding to less than 0.0048 mg ICG/kg body weight of the subject.

3. The method of claim 1, wherein the first bolus comprises an amount of the first fluorescence imaging agent corresponding to less than 0.004 mg ICG/kg body weight of the subject.

4. The method of claim 1, wherein the first bolus comprises an amount of the first fluorescence imaging agent corresponding to less than 0.003 mg ICG/kg body weight of the subject.

5. The method of claim 1, wherein the first bolus comprises an amount of the first fluorescence imaging agent corresponding to less than 0.002 mg ICG/kg body weight of the subject.

6. The method of claim 1, wherein the first bolus comprises an amount of the first fluorescence imaging agent corresponding to less than 0.001 mg ICG/kg body weight of the subject.

7. The method of claim 1, wherein the first bolus comprises an amount of the first fluorescence imaging agent corresponding to between 0.0001 and 0.0048 mg ICG/kg body weight per bolus, or between 0.001 and 0.0048 mg ICG/kg body weight per bolus.

8. The method of claim 1, wherein administering the first fluorescence imaging agent comprises injection by a controllable injection pump.

9. The method of claim 1, wherein the predefined time between the subsequent boluses is a regular time between the subsequent boluses.

10. The method of claim 1, wherein administering the first fluorescence imaging agent comprises injection of a series of at least 3, or at least 5, subsequent boluses with a predefined time of between 30 and 600 seconds, or between 60 and 600 seconds, or between 120 and 600 seconds, between the subsequent boluses.

11. The method of claim 1, wherein administering the first fluorescence imaging agent comprises injection of a series of at least 10 subsequent boluses with a predefined time of between 30 and 600 second, or between 60 and 600 seconds, or between 120 and 600 seconds, or between 60 and 300 seconds, between each of the subsequent boluses.

12. The method of claim 1, wherein fluorescence emission by the first fluorescence imaging agent from the anatomical structure is measured following administering the first bolus.

13. The method of claim 1, wherein each of the subsequent boluses of the series of subsequent boluses comprises a subsequent amount of the first fluorescence imaging agent which is an incremental increase or an incremental decrease compared to the amount of the first fluorescence imaging agent in a previous bolus.

14. The method of claim 13, wherein an initial amount of the first fluorescence imaging agent corresponds to at least 0.001 mg ICG/kg body weight of the subject and less than 0.005 mg ICG/kg body weight of the subject and wherein each of the subsequent boluses of the series of subsequent boluses comprises a subsequent amount of the first fluorescence imaging agent which is an incremental increase or an incremental decrease corresponding to between at least 0.001 mg ICG/kg body weight of the subject compared to the amount of the first fluorescence imaging agent in a previous bolus.

15. The method of claim 13, wherein an initial amount of the first fluorescence imaging agent corresponds to less than 0.0048 mg ICG/kg body weight of the subject and wherein each of the subsequent boluses of the series of subsequent boluses comprises a subsequent amount of the first fluorescence imaging agent which is an incremental increase or an incremental decrease corresponding to between 0.001 and 0.0048 mg ICG/kg body weight of the subject compared to the amount of the first fluorescence imaging agent in a previous bolus.

16. The method of claim 1, wherein the anatomical structure is the gastrointestinal tract, including the buccal cavity; pharynx; the small intestine including duodenum, jejunum, and ileum; the stomach, including esophagus, cardia, and pylorus; the large intestine including cecum, colon, rectum and the anal canal.

17. The method of claim 1, wherein the anatomical structure is an internal organ of the subject, wherein the anatomical structure is the skin of the subject, or wherein the anatomical structure comprises a wound which is the subject of the perfusion assessment.

18. The method of claim 1, wherein the fluorescence imaging agent comprises indocyanine green (ICG), fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof.

19. The method of claim 1, wherein the perfusion assessment comprises localizing a perfusion complication in the anatomical structure.

20. The method of claim 1, wherein the perfusion assessment is used in connection with a diagnostic or surgical procedure.

21. The method according to claim 20, wherein the diagnostic or surgical procedure comprises diagnostic laparoscopy, explorative laparoscopy, surgical laparoscopy with traditional laparoscopy, robotic surgery, intestinal anastomosis or open surgery.

* * * * *